US008592163B2

(12) United States Patent
Schlesinger et al.

(10) Patent No.: US 8,592,163 B2
(45) Date of Patent: Nov. 26, 2013

(54) METHOD OF DETERMINING IMMUNE ENHANCEMENT OF VIRUS INFECTIVITY USING FC RECEPTOR-TRANSFECTED CELL LINES

(75) Inventors: Jacob J. Schlesinger, Pittsford, NY (US); Xia Jin, Fairport, NY (US); Robert C. Rose, Dansville, NY (US); W. W. Shanaka Rodrigo, Rochester, NY (US)

(73) Assignee: University of Rochester, Rochester, NY (US)

( * ) Notice: Subject to any disclaimer, the term of this patent is extended or adjusted under 35 U.S.C. 154(b) by 1017 days.

(21) Appl. No.: 11/916,149

(22) PCT Filed: May 31, 2006

(86) PCT No.: PCT/US2006/020994
§ 371 (c)(1),
(2), (4) Date: Jul. 11, 2008

(87) PCT Pub. No.: WO2006/130621
PCT Pub. Date: Dec. 7, 2006

(65) Prior Publication Data
US 2010/0190147 A1 Jul. 29, 2010

Related U.S. Application Data

(60) Provisional application No. 60/685,817, filed on May 31, 2005.

(51) Int. Cl.
*G01N 33/53* (2006.01)
*A61K 39/12* (2006.01)

(52) U.S. Cl.
USPC ........................ 435/7.1; 424/130.1; 424/218.1

(58) Field of Classification Search
None
See application file for complete search history.

(56) References Cited

U.S. PATENT DOCUMENTS 6,060,273 A * 5/2000 Dirks et al. ................. 435/69.1

OTHER PUBLICATIONS

Talarmin et al., Journal of Clinical Microbiology, 1998, 36(5):1189-1192.*
Bakema et al., The Journal of Immunology, 2006, 176:3603-3610.*
Mady et al., Am. J. Immunol. 147(9):3139-3144 (1991).
Edelman, J. Infect. Dis. 191:650-653 (2005).
Kitchener et al., Vaccine 5696:4-7 (2005).
Sun et al., J. Infect. Dis. 193:1658-1665 (2006).
Edelman et al., Am. J. Trop. Med. Hyg 69(6):48-60 (2003).
Blaney et al., J. Virol. 79(9):5516-5528 (2005).
Guirakhoo et al., Virology 298:146-159 (2002).
Eckels et al., J. Immunol. 135(6):4201-4203 (1985).
Kliks et al., Am. J. Trop. Med. Hyg. 40(4):444-451 (1989).
Wu et al., Nature Medicine 6(7):816-820 (2000).
Vaughn et al., J. Infect. Dis. 181:2-9 (2000).
Schlesinger et al., Virology 260:84-88 (1999).
Littaua et al., J. Immunol. 144:3183-3186 (1990).
Libraty et al., J. Virol. 75(8):3501-3508 (2001).
Kontny et al., J. Virol. 62(11):3928-3933 (1988).
Peiris et al., J. Virol. 57:119-125 (1981).
Morens et al., J. Clin. Microbiol. 22(2):250-254 (1985).
Halstead, Reviews of Infectious Diseases 11(4):5830-5839 (1989).
Smith et al., Science 304:237-242 (2004).
Parren et al., Adv. Immunol. 77:195-262 (2001).
Martinez-Salas, Curr. Opin. Biotechnol. 10:458-464 (1999).
Hennecke et al., Nucl. Acids Res. 29(16):3327-3334 (2001).
Van de Winkel et al., J. Leukocyte Biol. 49:511-524 (1991).
Warmfrdam et al., Immunobiology 185:175-182 (1992).
Takai, Nature Reviews 2:580-592 (2002).
Duchemin et al., J. Biol. Chem. 269(16):12111-12117 (1994).
Fanger et al., J. Immunol. 157(2):541-548 (1996).
Fitzer-Attas et al., J. Exp. Med. 191(4):669-681 (2000).
Letourneur et al., J. Immunol. 147(8):2652-2656 (1991).
Miller et al., J. Exp. Med. 183:2227-2233 (1996).
Van den Herik-Oudijk et al., Blood 85(8):2202-2211 (1995).
Van den Herik-Oudijk et al., Blood 86(9):3302-3307 (1995).
Van Vugt et al., Blood 87(9):3593-3599 (1996).
Daeron, Annu. Rev. Immunol., 15:203-234 (1997).
Yang et al., "Distinct Cellular Interactions of Secreted and Transmembrane Ebola Virus Glycoproteins," Science 279:1034-1037 (1998).
Rodrigo et al., "Differential Enhancement of Dengue Virus Immune complex Infectivity Mediated by Signaling-Competent and Signaling-Competent and Signaling-Incompetent Human FcGammaRIA (CD64) or FcGammaRIIA (CD32)," J. Virol. 80(20):10128-10138, (2006).
Falgout et al., "Immunization of Mice with Recombinant Vaccinia Virus Expressing Authentic Dengue Virus Nonstructural Protein NS1 Protects Against Lethal Dengue Virus Encephalitis," J. Virol. 64(9):4356-4363 (1990).
Examination Report for corresponding AU Patent Application 2006252637, dated Nov. 5, 2010.
Supplementary Search Report for corresponding EP Patent Application 06760565.9, dated Oct. 21, 2010.

* cited by examiner

*Primary Examiner* — Stacy B. Chen
(74) *Attorney, Agent, or Firm* — LeClairRyan, a Professional Corporation

(57) ABSTRACT

The present invention relates to a method of detecting immune enhancement of virus infectivity, a method of determining neutralization and immune enhancement of virus infectivity, a method of identifying a virus epitope that displays immune enhancement, a method of identifying a compound that modulates activity of an Fc receptor, and a method of identifying a compound that modulates intracellular signaling of an Fc receptor. DNA constructs, cells, and kits relating to these assays are also disclosed.

27 Claims, 16 Drawing Sheets

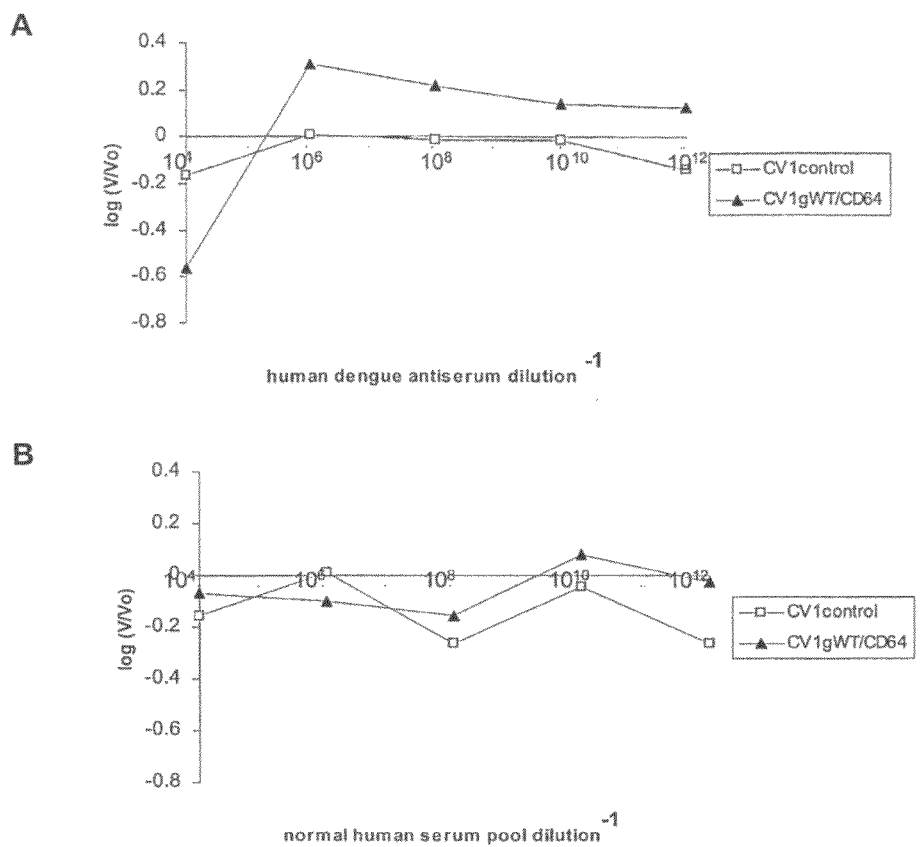
Figures 17A–B
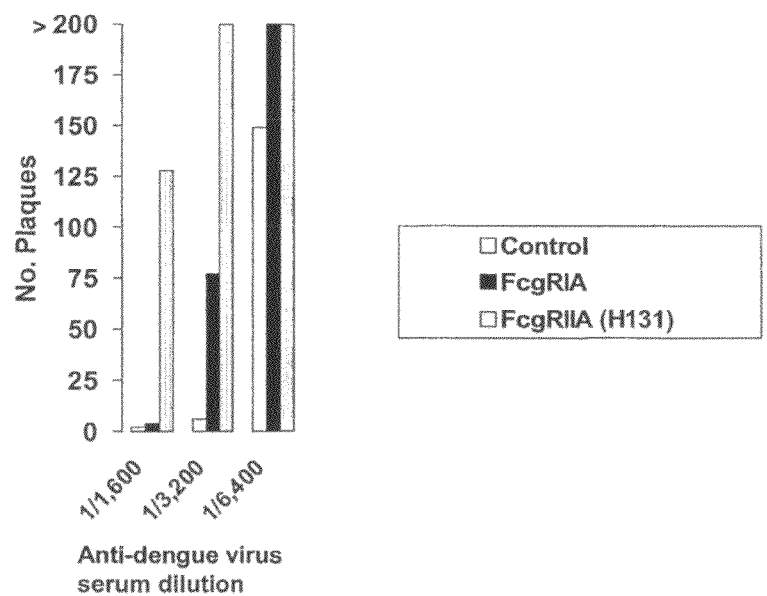
Figure 18

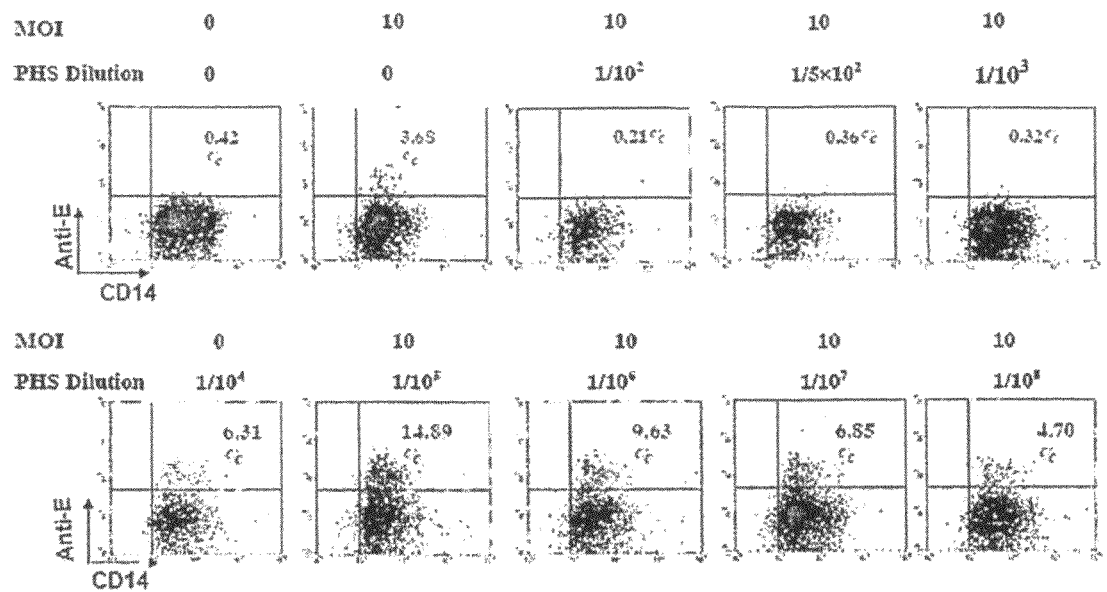
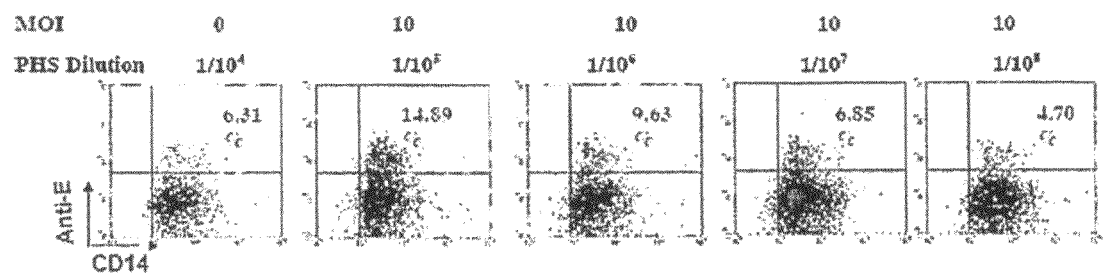
Figure 21
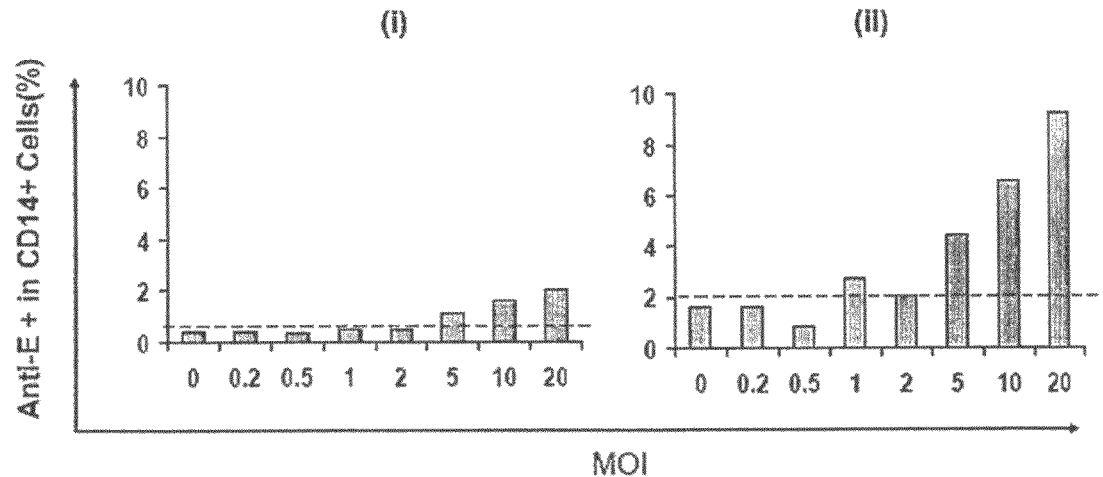
Figure 22

SEQUENCE LISTING

```
<160> NUMBER OF SEQ ID NOS: 2

<210> SEQ ID NO 1
<211> LENGTH: 27
<212> TYPE: PRT
<213> ORGANISM: Artificial
<220> FEATURE:
<223> OTHER INFORMATION: Homo sapiens Fc-gamma RIIA cytoplasmic tail
      immunoreceptor tyrosine activation motif

<400> SEQUENCE: 1

Tyr Glu Thr Ala Asp Gly Gly Tyr Met Ile Leu Asn Pro Arg Ala Pro
1               5                   10                  15

Thr Asp Asp Asp Lys Asn Ile Tyr Leu Thr Leu
            20                  25

<210> SEQ ID NO 2
<211> LENGTH: 22
<212> TYPE: PRT
<213> ORGANISM: Artificial
<220> FEATURE:
<223> OTHER INFORMATION: Homo sapiens Fc-gamma RIA gamma chain

<400> SEQUENCE: 2

Tyr Glu Lys Ser Asp Gly Val Tyr Thr Gly Leu Ser Thr Arg Asn Gln
1               5                   10                  15

Glu Thr Tyr Glu Thr Leu
            20
```

METHOD OF DETERMINING IMMUNE ENHANCEMENT OF VIRUS INFECTIVITY USING FC RECEPTOR-TRANSFECTED CELL LINES

This application is a national stage application under 35 U.S.C. 371 of PCT/US06/20944, filed May 31, 2006, and claims the benefit of U.S. Provisional Patent Application Ser. No. 60/685,817, filed May 31, 2005, which is hereby incorporated by reference in its entirety.

FIELD OF THE INVENTION

The present invention is directed, generally, to human Fc receptor-transfected cells and cell lines, and their use in detecting virus-neutralizing and immune-enhancing antibodies.

BACKGROUND OF THE INVENTION

The interaction between virus and antibody ordinarily leads to neutralization, but infectivity of some antibody-coated viruses may be enhanced if susceptible cells bear Fcγ receptors (FcγR). While this apparent paradox has been demonstrated for a number of viruses, it is of particular interest with respect to the dengue viruses. Severe forms of dengue fever, manifested by heightened viremia levels and generalized microvascular leak syndromes (Vaughn et al., "Dengue Viremia Titer, Antibody Response Pattern, and Virus Serotype Correlate with Disease Severity," *J Infect Dis* 181(1):2-9 (2000)), have been linked to enhanced infection of monocyte/macrophages by dengue immune complexes (Halstead, S. B., "Antibody, Macrophages, Dengue Virus Infection, Shock, and Hemorrhage: A Pathogenetic Cascade," *Rev Infect Dis* 11(Suppl 4):S830-9 (1989); Kliks et al., "Antibody-dependent Enhancement of Dengue Virus Growth in Human Monocytes as a Risk Factor for Dengue Hemorrhagic Fever," *Am J Trop Med Hyg* 40(4):444-51 (1989)). Potentially life-threatening forms of dengue fever emerge most often in the course of dengue epidemics when new dengue serotypes (particularly dengue-2) are sequentially introduced into a region. Persuasive seroepidemiologic evidence, clinical cohort studies, and monkey experiments, link pre-existing dengue antibodies, acquired from earlier dengue infection or passively through maternal transmission, to heightened viremia and more severe disease (Halstead, S. B., "Antibody, Macrophages, Dengue Virus Infection, Shock, and Hemorrhage: A Pathogenetic Cascade," *Rev Infect Dis* 11(Suppl 4):S830-9 (1989); Halstead, S. B., "Pathogenesis of Dengue: Challenges to Molecular Biology," *Science* 239:476-481 (1988); Kliks et al., "Evidence that Maternal Dengue Antibodies are Important in the Development of Dengue Hemorrhagic Fever in Infants," *Am J Trop Med Hyg* 38:411-419 (1988); Kliks et al., "Antibody-dependent Enhancement of Dengue Virus Growth in Human Monocytes as a Risk Factor for Dengue Hemorrhagic Fever," *Am J Trop Med Hyg* 40(4):444-51 (1989); Vaughn et al., "Dengue Viremia Titer, Antibody Response Pattern, and Virus Serotype Correlate with Disease Severity," *J Infect Dis* 181(1):2-9 (2000)).

Several promising multivalent dengue vaccine candidates are in late phases of clinical trial, mainly in dengue-free locales (Halstead & Deen, "The Future of Dengue Vaccines," *Lancet* 360:1243-5 (2002)). Their future evaluation in dengue endemic environments poses a unique potential hazard: if the quality of the antibody response to a vaccine component were suboptimal, or if vaccine-stimulated protective antibody levels were to wane, naturally-acquired dengue infection of increased severity might follow.

The nature of enhancing antibodies has been widely investigated using primary monocyte/macrophages or macrophage-like cell lines that express FcγR. Receptor properties that might affect immune enhancement, however, have received comparatively much less attention, largely because heterogeneous FcγR display on such cells complicates interpretation of experimental results.

Enhanced infection of Fc receptor (FcR)-bearing cells of macrophage/monocyte lineage by antibody-complexed dengue virus is central to the pathogenesis of serious forms of dengue fever. Cultured peripheral blood macrophages and macrophage-like cell lines have typically been used to characterize antibodies with respect to enhancing capacity, but results with such cells are confounded by the simultaneous and variable expression of multiple FcR classes and isoforms of differing physiology and by potential ambiguities that arise when antibody and FcR are not of the same species origin. An added problem is failure of dengue virus to form plaques in such cells, so that surrogate amplification methods are needed to measure virus replication. The immune enhancement phenomenon may also be clinically relevant to the pathogenesis of a variety of unrelated RNA and DNA viruses of medical importance.

FcγR comprise a multi-gene family of integral membrane glycoproteins that exhibit complex activation or inhibitory effects on cell functions after aggregation by complexed IgG (Ravetch & Bolland, "IgG Fc Receptors," *Annu Rev Immunol* 19:275-90 (2001); Takai, T., "Roles of Fc Receptors in Autoimmunity," *Nat Rev Immunol* 2(8):580-92 (2002); Nimmerjahn & Ravetch, "Fcγ Receptors: Old Friends and New Family Members," *Immunity* 24:19-28 (2006)). Two activatory human FcγR of different classes and with distinctive, but overlapping, distribution among monocytes known to be permissive to dengue virus infection have been examined. The first, FcγRIA (CD64), is a 72 kD protein found exclusively on antigen-presenting cells of macrophage and dendritic cell lineages, most of which are permissive to dengue virus replication (Fanger et al., "Type I (CD64) and Type II (CD32) Fcγ Receptor-mediated Phagocytosis by Human Blood Dendritic Cells," *J Immunol* 157(2):541-8 (1996); Libraty et al., "Human Dendritic Cells are Activated by Dengue Virus Infection: Enhancement by Gamma Interferon and Implications for Disease Pathogenesis," *J Virol* 75(8):3501-8 (2001); Wu et al., "Human Skin Langerhans Cells are Targets of Dengue Virus Infection," *Nat Med* 6(7):816-20 (2000)). FcγRIA exhibits high affinity for monomeric IgG1 and exists bound to this immunoglobulin in vivo. The second, FcγRIIA (CD32), is a 40 kD protein unique to humans and more broadly distributed among a variety of myelogenous cell types. It has low affinity for monomeric IgG, preferentially binding multivalent IgG (Maenaka et al., "The Human Low Affinity Fcγ Receptors IIa, IIb, and III Bind IgG with Fast Kinetics and Distinct Thermodynamic Properties," *J Biol Chem* 276(48):44898-904 (2001)). Each FcγR is comprised of three portions: an extracellular portion of two (FcγRIIA) or three (FcγRIA) IgG-like domains, a short hydrophobic transmembrane region, and a cytoplasmic tail. A conserved immunoreceptor tyrosine-based activation motif (ITAM) links each FcγR to tyrosine kinase-activated signaling pathways that modulate cell metabolism and physical behavior when triggered by receptor clustering (Duchemin et al., "Clustering of the High Affinity Fc Receptor for Immunoglobulin G (FcγRI) Results in Phosphorylation of its Associated γ-Chain," *J Biol Chem* 269(16):12111-7 (1994); Letourneur et al., "Characterization of the Family of Dimers Associated with Fc Receptors (FcεRI and FcγRIII)," *J Immunol* 147(8):2652-6 (1991); Van den Herik-Oudijk et al., "Functional Differences Between Two Fc Receptor ITAM Signaling Motifs," *Blood* 86(9):3302-7 (1995); Van den Herik-Oudijk et al., "Functional Analysis of Human FcγRII (CD32) Isoforms Expressed in B Lymphocytes," *J Immunol* 152(2):574-85 (1994)). FcγRIA acquires this function by non-covalent association with the γ-chain subunit, a short (ca. 11 kD) transmembrane ITAM-containing homodimer (Kwiatkowska & Sobota, "The Clustered Fcγ Receptor II is Recruited to Lyn-containing Membrane Domains and Undergoes Phosphorylation in a Cholesterol-dependent Manner," *Eur J Immunol* 31(4):989-98 (2001)). FcγRIIA, unlike other Fc receptors and most immunoreceptors, incorporates the ITAM in its ligand binding chain.

Signal transduction triggered by ligand engagement is intimately involved in the phagocytosis of IgG opsonized particles where the molecular details of FcγRIA and FcγRIIA signaling have been revealed in exquisite detail (Fitzer-Attas et al., "Fcγ Receptor-mediated Phagocytosis in Macrophages Lacking the Src Family Tyrosine Kinases Hck, Fgr, and Lyn," *J Exp Med* 191(4):669-81 (2000); Kim et al., "Fcγ Receptor Transmembrane Domains: Role in Cell Surface Expression, γ Chain Interaction, and Phagocytosis," *Blood* 101(11):4479-84 (2003); Kim et al., "Fcγ Receptors Differ in Their Structural Requirements for Interaction with the Tyrosine Kinase Syk in the Initial Steps of Signaling for Phagocytosis," *Clin Immunol* 98(1):125-32 (2001); Lowry et al., "Functional Separation of Pseudopod Extension and Particle Internalization During Fcγ Receptor-mediated Phagocytosis," *J Exp Med* 187(2):161-76 (1998); Van den Herik-Oudijk et al., "Functional Differences Between Two Fc Receptor ITAM Signaling Motifs," *Blood* 86(9):3302-7 (1995)). A signaling requirement for entry of infectious virus immune complexes following FcγR engagement is less certain and has been little studied. One view is that FcγR may facilitate entry of dengue immune complexes by simply concentrating them onto a putative dengue receptor, in essence a passive effect that leads to internalization and infection, perhaps uninfluenced by FcγR signal transduction (Mady et al., "Antibody-dependent Enhancement of Dengue Virus Infection Mediated by Bispecific Antibodies Against Cell Surface Molecules Other Than Fcγ Receptors," *J Immunol* 147(9):3139-44 (1991)). Conversely, evidence of differential immune enhancement among FcγR, or for modulation of dengue immune complex infectivity by FcγR-triggered signaling, would have important implications with respect to mechanisms of dengue neutralization and dengue fever pathogenesis.

FcγRIA and FcγRIIA have previously been shown to facilitate antibody-mediated dengue enhancement in human macrophage-like cells using surrogate plaque assays to measure virus replication (Kontny et al., "Gamma Interferon Augments Fcγ Receptor-mediated Dengue Virus Infection of Human Monocytic Cells," *J Virol* 62(11):3928-33 (1988); Littaua et al., "Human IgG Fc Receptor II Mediates Antibody-dependent Enhancement of Dengue Virus Infection," *J Immunol* 144(8):3183-6 (1990)) since dengue virus does not form plaques in such cells (Peiris & Porterfield, "Antibody-dependent Enhancement of Plaque Formation on Cell Lines of Macrophage Origin—A Sensitive Assay for Antiviral Antibody," *J Gen Virol* 57(Pt. 1):119-25 (1981)). A direct assay would help in elucidating the role of various contributors to antibody-dependent enhancement.

A balanced antibody response to multivalent dengue vaccines has not been achieved (Edelman, R., "Dengue and Dengue Vaccines," *JID* 191:650-653 (2005); Kitchener et al., "Immunogenicity and Safety of Two Live-attenuated Tetravalent Dengue Vaccine Formulations in Healthy Australian Adults," *Vaccine* 24(9):1238-41 (2006); Sun et al., "Protection of Rhesus Monkeys Against Dengue Virus Challenge after Tetravalent Live Attenuated Dengue Virus Vaccination," *JID* 193:1658-1665 (2006); Edelman et al., "Phase I Trial of 16 Formulations of a Tetravalent Live-attenuated Dengue Vaccine," *Am J Trop Med Hyg* 69(Suppl 6):48-60 (2003); Blaney, Jr. et al., "Recombinant, Live-attenuated Tetravalent Dengue Virus Vaccine Formulations Induce a Balanced, Broad, and Protective Neutralizing Antibody Response Against Each of the Four Serotypes in Rhesus Monkeys," *J Virol* 79(9):5516-5528 (2005); Guirakhoo et al., "Viremia and Immunogenicity in Nonhuman Primates of a Tetravalent Yellow Fever-Dengue Chimeric Vaccine Genetic Reconstructions, Dose Adjustment, and Antibody Responses against Wild-type Dengue Virus Isolates," *Virol* 298:146-159 (2002)). An assay that could be used to screen for neutralization and/or enhancement by candidate vaccines would be helpful in vaccine development.

The present invention is directed to overcoming these and other deficiencies in the art.

SUMMARY OF THE INVENTION

A first aspect of the present invention relates to a method of determining immune enhancement of virus infectivity. This method involves exposing a first virion-antibody mixture that includes virion-antibody complexes to a first set of cells, where the cells include a recombinant Fc receptor competent for both binding and uptake of virion-antibody complexes. The infectivity of the first virion-antibody mixture in the first set of cells is measured, and an infectivity standard is provided. The measured infectivity is compared to the infectivity standard, where an increase in infectivity relative to the infectivity standard indicates that antibodies in the first virion-antibody mixture promote immune enhancement.

A second aspect of the present invention relates to a method of determining neutralization and immune enhancement of virus infectivity. This method involves determining immune enhancement of virus infectivity by performing the method according to the first aspect of the present invention, providing a second infectivity standard, and comparing the measured infectivity to the second infectivity standard. A decrease in infectivity relative to the second infectivity standard indicates that antibodies in the first virion-antibody mixture neutralize virus infectivity.

A third aspect of the present invention relates to a method of identifying a virus epitope implicated in immune enhancement of virus infectivity. This method involves exposing first virion-antibody complexes to a first set of cells, where the cells include a recombinant Fc receptor competent for both binding and uptake of virion-antibody complexes and the antibodies bind specifically to the virus epitope to form the virion-antibody complexes. Infectivity of the first virion-antibody complexes in the first set of cells is measured. An infectivity standard is provided, and the measured infectivity is compared to the infectivity standard. An increase in infectivity relative to the infectivity standard indicates that the virus epitope recognized by the antibody is implicated in immune enhancement of virus infectivity.

A fourth aspect of the present invention relates to a method of identifying a compound that modulates activity of an Fc receptor. This method involves exposing first virion-antibody complexes to a first set of cells in the presence of a test compound, where the cells include a recombinant Fc receptor competent for both binding and uptake of the first virion-antibody complexes. Infectivity of the first virion-antibody complexes in the first set of cells is measured. An infectivity standard is provided, and the measured infectivity is compared to the infectivity standard. An increase in infectivity relative to the infectivity standard indicates that the test compound increases activity of the Fc receptor, and a decrease in infectivity relative to the infectivity standard indicates that the test compound decreases activity of the Fc receptor.

A fifth aspect of the present invention relates to a method of identifying a compound that modulates intracellular signaling of an Fc receptor. This method involves exposing virion-antibody complexes to a first set of cells in the presence of a test compound, where the cells of the first set include a recombinant Fc receptor that is competent for both binding and uptake of the virion-antibody complexes and competent for signaling-dependent mediation of immune enhancement of the virion-antibody complexes. Substantially similar virion-antibody complexes are exposed to a second set of cells in the presence of the test compound, where the cells of the second set include a signaling-incompetent form of the Fc receptor. Infectivity of the virion-antibody complexes in the first and second sets of cells is measured, and the two measurements are compared. Substantially the same infectivity in the second set of cells relative to the first set of cells indicates that the test compound decreases intracellular signaling of the Fc receptor.

A sixth aspect of the present invention relates to DNA constructs for preparing the recombinant cells useful in the above-identified assays. According to one embodiment, the DNA constructs include a first DNA molecule that has a nucleotide sequence that encodes an Fc receptor γ-chain polypeptide, and a second DNA molecule that has a nucleotide sequence that encodes an Fc receptor α-subunit.

A seventh aspect of the present invention relates to a cell useful in the above-identified assays. According to one embodiment, the cell includes a mutant Fc receptor competent for binding to a virion-antibody complex but defective for signaling.

An eighth aspect of the present invention relates to one or more kits for performing the methods of the present invention. The kits of the present invention can include one or more cells or cell lines of the present invention, as well as any combination of one or more of cell culture plates, control (mock-transfected) cells, control (non-immune) sera, cell culture media, virion, labeling antibodies (including fluorochrome detection antibodies for flow cytometry, and enzyme-conjugated antibodies), and instructions for carrying out any assay of the present invention.

The assays of the present invention are useful, inter alia, for screening for neutralization and/or enhancement of viral infectivity, for elucidating the role of agents or viral epitopes that are involved in these effects, and to verify the acceptable neutralizing antibody profile in vaccine recipients. For example, the relative efficiency with which FcγRIA and FcγRIIA individually enhances dengue immune complex infectivity, and whether signal transduction competency plays a role, has been examined. The strategy to answer these fundamental questions surrounding the immune enhancement phenomenon involved expression of native and mutant forms of human γ-chain/FcγRIA and FcγRIIA in dengue-permissive COS cells in which dengue virus immune enhancement was directly measured by conventional plaque assay. The infectivity of dengue immune complexes was found to be strikingly greater after engagement of FcγRIIA than FcγRIA, and signaling competency was found to be required for optimally enhanced infectivity subserved by FcγRIA but apparently not by FcγRIIA. The assays of the present invention can be used to screen candidate vaccines or passive antibody therapies for their ability to induce unintended enhancement of viral infectivity.

BRIEF DESCRIPTION OF THE DRAWINGS

In FIG. 9B, phagocytosis is expressed as the phagocytic index, the number of internalized yeast particles per 100 FcγR-expressing COS cells. P values: a) THP-1 vs. $\gamma^{WT}$/FcγRIA or FcγRIIA$^{WT}$, b) $\gamma^{3\times MUT}$/FcγRIA vs. $\gamma^{WT}$/FcγRIA; c) FcγRIIA$^{3\times MUT}$ vs. FcγRIIA$^{WT}$. Results are the mean and standard deviation of three individual experiments with FcγRIA and four individual experiments with FcγRIIA, performed in duplicate.

In FIGS. 10B and 10C, virus-antibody complexes, prepared with serially diluted human dengue antiserum and dengue 2 (16681 (FIG. 10B) or NGC (FIG. 10C)), were added to signaling-competent ($\gamma^{WT}$/FcγRIA; FcγRIIA$^{WT}$) or signaling-incompetent ($\gamma^{3\times MUT}$/FcγRIA; $\gamma^{STP}$/FcγRIIA; FcγRIIA$^{3\times MUT}$) Fc receptor-expressing COS cells. COS cells expressing γ-chain only ($\gamma^{WT}$/FcγRIA$^{STP}$) or cells transfected with the empty pcDNA5/FRT vector served as negative controls. Plaques were detected by indirect immunostaining with a dengue 2 NS1-specific monoclonal antibody. Results are representative of 10 individual experiments performed in duplicate or triplicate.

In FIG. 11A, dengue 2 virus (16681) immune complexes were prepared by incubating virus at a single multiplicity of infection (MOI) (0.025) with serially diluted human dengue antiserum. In FIG. 11B, immune complexes prepared with a single antibody dilution (1/1,000) and serial virus MOI were added to signaling-competent ($\gamma^{WT}$/FcγRIA; FcγRIIA$^{WT}$) or signaling-incompetent ($\gamma^{3\times MUT}$/FcγRIA; FcγRIIA$^{3\times MUT}$) Fc receptor-expressing COS cells. Cells expressing γ-chain only ($\gamma^{WT}$/FcγRIA$^{STP}$) or those transfected with the pcDNA5/FRT vector served as negative controls. Plaques were detected by indirect immunostaining with a dengue 2 NS1-specific monoclonal antibody. For FcγRIIA, plaques corresponding to MOI 0.5 were too numerous to count. P values were determined using a two-tailed t-test: a) $\gamma^{WT}$/FcγRIA vs. $\gamma^{3\times MUT}$/FcγRIA; b) $\gamma^{3\times MUT}$/FcγRIA vs. $\gamma^{WT}$/FcγRIA$^{STP}$ and vector controls. Results are the mean and standard deviation of an experiment performed in quadruplicate, and are representative of three individual experiments performed in triplicate or quadruplicate.

As shown in FIG. 12A, γ-chain abundance was determined by Western blot: solubilized lysates prepared from $2.5 \times 10^5$ cells of each COS transfectant were electrophoresed and subjected to Western blot using a monospecific rabbit serum against human γ-chain (Letourneur et al., "Characterization of the Family of Dimers Associated with Fc Receptors (FcεRI and FcγRIII)," *J Immunol* 147(8):2652-6 (1991), which is hereby incorporated by reference in its entirety). FIG. 12B is a graph of phagocytosis of opsonized yeast particles by COS cells transfected with γ-chain/FcγRIA versions or FcγRIA only. COS cells transfected with an empty vector or expressing γ-chain only ($\gamma^{WT}$/FcγRIA$^{STP}$) served as controls. The phagocytic index was defined as the number of yeast particles internalized by 100 FcγRIA-expressing COS cells. In parallel, the respective COS transfectants were incubated with dengue 2 (16681) immune complexes formed with pooled human dengue antiserum (1/1,000) and serial concentrations of dengue virus; results of an experiment performed in triplicate with a virus MOI 1.0 is shown in FIG. 12C. Two-tailed t-test P values compared immune complex infectivity with each FcγRIA construct to that of $\gamma^{WT}$/FcγRIA: *P<0.05; † P<0.01. FIG. 12D is a graph showing the correlation between phagocytosis and infectivity of dengue immune complexes formed with dengue antisera (1/1,000 dilution) and dengue MOI 0.25 (a), 0.50 (b), and 1.0 (c). Linear regression analysis (R) was performed using Microsoft Excel software.

FIGS. 17A-B are graphs demonstrating antibody-mediated enhancement of strain 16681 dengue 2 virus in a stable CV-1 cell line that constitutively expresses $\gamma^{WT}$/FcγRIA (CD64). For the data shown in FIG. 17A, immune complexes were prepared by mixing $10^3$ PFU/mL dengue 2 virus (strain 16681) with serial 100-fold dilutions of pooled human dengue antiserum ($1/10^4$ to $1/10^{12}$) and transferred onto pre-formed cell monolayers. CV-1 "empty" vector served as the negative control. Plaques were developed by indirect immunostaining with a dengue NS-1 specific monoclonal antibody (mAb 9A9). X-axis values are serum dilution reciprocals; Y-axis values are Log ($V/V_o$) where V refers to the number of plaques/well in the presence of antibody normalized against $V_o$, the number of plaques/well in the absence of antibody. For the data shown in FIG. 17B, pooled normal human serum was used as a control in parallel assays. Results are the means of quadruplicate (FIG. 17A) or duplicate (FIG. 17B) plaque readings and are representative of four individual experiments.

FIG. 18 is a graph of plaque formation by human antibody-complexed dengue 2 virus in human FcγR-expressing CV-1 cell lines. Control CV-1/FRT cells, open bar; FcγRIA, closed bar; FcγRIIA (allotype H131), hatched bar.

FIG. 21 is a series of flow cytometry dot plots of representative results of antibody-dependent enhancement of Dengue virus infection in primary human monocytes. Freshly isolated human peripheral blood mononuclear cells were infected by Dengue virus 2 strain 16681 at multiplicity of infection (MOI) of 10 in the absence or presence of pooled human serum (PHS) at varying dilutions for two days, then harvested and stained by labeled monoclonal antibodies to Dengue virus 2 envelope E protein or an isotype-matched IgG control, as well as antibodies to T cells (CD3) or monocytes/macrophages (CD14), then analyzed using flow cytometry. Analyses show staining percentages of anti-E antibody and CD14 antibody for each of the conditions. This representative graph shows no infection (0.42%), Dengue virus infection (3.68%), neutralization (0.21, 0.36 and 0.32%), and antibody-dependent enhancement (6.31, 14.89, 9.63, 6.85 and 4.70%).

FIG. 22 is a set of graphs of Dengue virus infection of primary human monocytes. Freshly isolated human peripheral blood mononuclear cells from two subjects (i and ii) were infected by Dengue virus 2 strain 16681 at varying MOI for two days, then harvested and stained by labeled monoclonal antibody to Dengue virus 2 envelope E protein or an isotype-matched IgG control, as well as antibodies to T cells (CD3) or monocytes/macrophages (CD14), then analyzed using flow cytometry. Results show the differences in staining percentages between anti-E antibody and control IgG at each of the conditions for CD14-positive and CD3-negative cells.

DETAILED DESCRIPTION OF THE INVENTION

Figure 1:
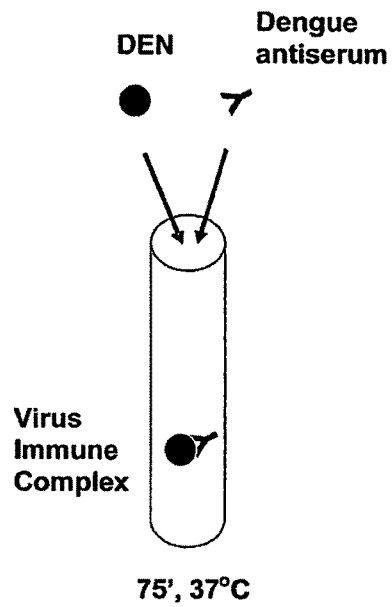
FIG. 1 is a schematic diagram illustrating the formation of virion-antibody complexes to be used in a representative simultaneous neutralization/enhancement assay of the present invention. Dengue virus virions ("DEN") are exposed to antiserum containing anti-Dengue virus antibodies, to form a virion-antibody mixture containing Dengue virion-antibody complexes. The recited conditions are exemplary.

One aspect of the present invention relates to a method of determining immune enhancement of virus infectivity that may be caused by antibodies that bind to epitopes on the surface of virion.

The methods of the present invention can be used to assess immune enhancement of virus infectivity for any virus that is capable of such immune enhancement, whether now known or later identified (Parren & Burton, "The Antiviral Activity of Antibodies in Vitro and in Vivo," *Adv Immunol* 77:195-262 (2001); Peiris & Porterfield, "Antibody-dependent Enhancement of Plaque Formation on Cell Lines of Macrophage Origin—A Sensitive Assay for Antiviral Antibody," *J Gen Virol* 57(Pt. 1):119-25 (1981); Halstead, "Immune Enhancement of Viral Infection," *Prog Allergy* 31:301-364 (1982); Morens, "Antibody-dependent Enhancement of Infection and the Pathogenesis of Viral Disease," *Clin Infec Dis* 19(3):500-512 (1994); Suhrbier & Linn, "Suppression of Antiviral Responses by Antibody-dependent Enhancement of Macrophage Infection," *Trends Immunol* 24:165-168 (2003); Burstin et al., "Infection of a Macrophage-like Cell Line, P388D1 with Reovirus; Effects of Immune Ascitic Fluids and Monoclonal Antibodies on Neutralization and on Enhancement of Viral Growth," *J Immunol* 130(6):2915-9 (1983); Hohdatsu et al., "A Study on the Mechanism of Antibody-dependent Enhancement of Feline Infectious Peritonitis Virus Infection in Feline Macrophages by Monoclonal Antibodies," *Arch Virol* 120(3-4):207-17 (1991); Olsen et al, "Monoclonal Antibodies to the Spike Protein of Feline Infectious Peritonitis Virus Mediate Antibody-dependent Enhancement of Infection of Feline Macrophages," *J Virol* 66(2):956-65 (1992), which are hereby incorporated by reference in their entirety). Exemplary viruses include, without limitation, viruses in the families Flaviviridae (e.g., Flavivirus), Togaviridae (e.g., Alphavirus), Retroviridae (e.g., Lentivirus), Orthomyxoviridae (e.g., Influenza viruses), Paramyxoviridae (e.g., Pneumovirus), Arenaviridae (e.g., Arenavirus), Bunyaviridae (e.g., Orthobunyavirus, Phleboviruses), Filoviridae (e.g., Filovirus), Rhabdoviridae (e.g., Lyssavirus), Picornaviridae (e.g., Enterovirus), Herpesviridae (e.g., Simplex viruses), Reoviridae (e.g., Orthoreovirus), and Coronaviridae (e.g., Coronavirus).

Specific Flaviviruses that can be used in the present invention include, without limitation, dengue viruses, West Nile virus, Japanese encephalitis virus, Kunjin virus, Murray Valley encephalitis virus, Uganda-S virus, yellow fever virus, Tick-borne encephalitis virus, hepatitis C virus, and Louping-ill virus.

Specific Alphaviruses that can be used in the present invention include, without limitation, Ross River virus, Semliki Forest virus, Sindbis virus, and Western equine encephalitis virus.

Specific Lentiviruses that can be used in the present invention include, without limitation, human immunodeficiency virus.

Specific Influenza viruses that can be used in the present invention include, without limitation, Influenza A and Influenza B viruses.

Specific Pneumoviruses that can be used in the present invention include, without limitation, respiratory syncytal virus.

Specific Arenaviruses that can be used in the present invention include, without limitation, Lassa virus and Pichinde virus.

Specific Orthobunyaviruses that can be used in the present invention include, without limitation, Bunyamwera virus and Lokern virus.

Specific Phleboviruses that can be used in the present invention include, without limitation, Rift Valley fever virus.

Specific Filoviruses that can be used in the present invention include, without limitation, Ebola virus.

Specific Lyssaviruses that can be used in the present invention include, without limitation, rabies virus.

Specific Enteroviruses that can be used in the present invention include, without limitation, polio virus and Coxsackie B3 virus.

Specific Simplex viruses that can be used in the present invention include, without limitation, human herpesvirus.

Specific Orthoreoviruses that can be used in the present invention include, without limitation, mammalian orthoreovirus.

Specific Coronaviruses that can be used in the present invention include, without limitation, feline infectious peritonitis virus.

The antibody to be screened in the assays of the present invention can be either polyclonal antiserum or a monoclonal antibody preparation.

The polyclonal antiserum can be a pooled antiserum (from multiple individuals, all exposed to the same active vaccine) or an antiserum from a single individual. Moreover, the antiserum can be treated to remove specific antibody sub-populations, rendering the polyclonal antiserum, for example, substantially monospecific.

In one embodiment, the antiserum is obtained from an immunized mammal, preferably a human, that has been inoculated against the same virion (type and/or strain) being tested. In another embodiment, the antiserum is obtained from an immunized mammal, preferably a human, that has been inoculated against a different virion from that being tested. Using antisera from mammals immunized against multiple viruses and/or immunized multiple times is also contemplated. In a still further embodiment, the antiserum is from an individual previously infected by a virus that is the same strain or a different strain from that being tested.

The monoclonal antibody preparation can include one or more monoclonal antibodies or functional fragments thereof, such as Fab fragments, $F(ab')_2$ fragments, and Fv fragments.

The antibody to be screened is the type of antibody that, having formed an immune complex with a virus, can bind to the type of Fc receptor that is recombinantly expressed by the recombinant cells that are used in accordance with the present invention. Thus, the antibody is an IgG antibody when the Fc receptor is an Fcγ receptor, the antibody is an IgA antibody when the Fc receptor is an Fcα receptor, etc.

The cell that expresses the recombinant Fc receptor can be any mammalian cell, whether derived from an established cell line or a primary cell isolated from an individual. Preferably the cell (prior to transfection) does not express a native Fc receptor. Suitable cells include, without limitation, monkey kidney cells, COS cells, CV-1 cells, Vero cells, LLC-MK2 cells, human adenocarcinoma SW13 cells, HeLa cells, endothelial cells, primary foreskin fibroblasts, liver Huh-7 cells, baby hamster kidney cells, and Chinese hamster ovary cells. The cells may be transiently or stably transfected with a recombinant DNA molecule encoding the relevant receptor, by any suitable method that will be apparent to one of skill in the art. In aspects of the present invention in which infectivity is measured using plaque assays, suitable cells are those in which the virion is capable of forming plaques (i.e., replicating and infecting adjacent cells).

The Fc receptor to be recombinantly expressed can be any Fc receptor or variant thereof that, under suitable conditions, mediates antibody-dependent enhancement of infectivity of the virion. The Fc receptor can be a wild-type receptor or a variant (mutant), as long as the variant is competent for binding and uptake of virion-antibody complexes. The Fc receptor can be either signaling-competent or signaling-incompetent. Suitable Fc receptors include, without limitation, FcαR, FcδR, FcγR, FcεR, Fcα/μ, and FcRn. Preferred Fcγ receptors include, without limitation, FcγRIA (CD64), FcγRIIA (CD32), FcγRIIIA (CD16), and FcγRIIB. The human Fcγ receptors have the amino acid sequences (and are encoded by nucleic acid sequences) as reported at Genbank Accession Nos.: AB025256, AF416711, AF433951, AF433952, X52473, X16863, X52645, U90938, U90939, U90940, U90941, L03419, L03420, J04162, L03418, M28697, and M28696, each of which is hereby incorporated by reference in its entirety.

Depending on the virion, it may be preferable for the recombinant cell to further include a viral receptor, i.e., other receptors that may be used by the virus to infect the cell. Suitable viral receptors for assays using HIV-1 virions include, for example, CD4, CXCR4, and CCR5 (Smith & Helenius, "How Viruses Enter Animal Cells," *Science* 304 (5668):237-42 (2004), which is hereby incorporated by reference in its entirety).

This method involves exposing a first virion-antibody mixture that includes virion-antibody complexes to a first set of cells, where the cells include a recombinant Fc receptor competent for both binding and uptake of virion-antibody complexes. The infectivity of the first virion-antibody mixture in the first set of cells is measured. The measured infectivity is compared to a provided infectivity standard, where an increase in infectivity relative to the standard indicates that antibodies in the first virion-antibody mixture promote immune enhancement of virus infectivity.

In accordance with the several embodiments described herein, virion-antibody mixtures can be prepared by exposing virion to an antiserum that includes one or more antibodies that recognize the virion or to an antiserum (control) that contains no antibodies that recognize the virion. Regardless, the step of exposing the virion and antiserum is carried out under conditions that are effective to allow for formation of virion-antibody complexes (if such antibodies are present).

The infectivity standard can be a statistically predetermined range of positive infections that one would expect to be measured under a particular experimental protocol. The standard can be set at a 95%, 97%, 98% or 99% confidence level. Alternatively, the infectivity standard can be an internal control performed in parallel with the test assay of the present invention. Basically, a second virion-antibody mixture is exposed to a second set of cells, and infectivity of the second virion-antibody mixture is measured in the second set of cells. The infectivity between the first and second set of cells can then be compared.

The use of internal controls is described in relation to the embodiments described below.

Figure 2:
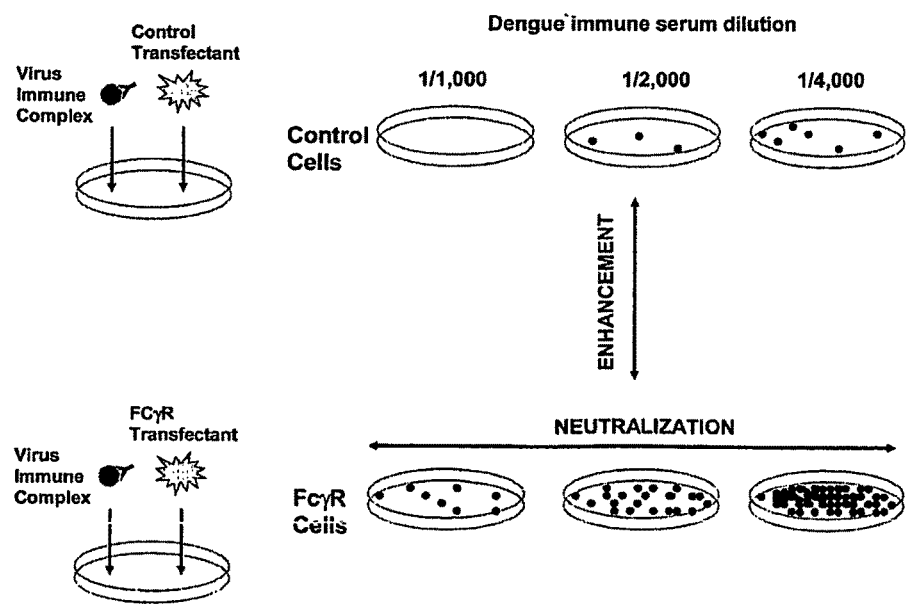
FIG. 2 is a schematic diagram illustrating a representative simultaneous neutralization/enhancement assay of the present invention. Virion-antibody complexes, formed as shown in FIG. 1 by exposing the virions to different dilutions of the antiserum, are contacted with cells expressing a recombinant Fcγ receptor ("FcγR Transfectant") and control cells that do not express the recombinant receptor ("Control Transfectant"), and plaques are allowed to form. Neutralization is assessed by comparing the infectivity in the FcγR-expressing cells at the various dilutions. A decrease in infectivity with a higher dilution relative to infectivity at a lower dilution would indicate that the antiserum contains neutralizing antibodies. Enhancement is assessed by comparing the infectivity in the FcγR-expressing cells relative to the control cells at a certain dilution. An increase in infectivity in the FcγR-expressing cells would indicate that the antiserum contains immune-enhancing antibodies.
Figure 3:
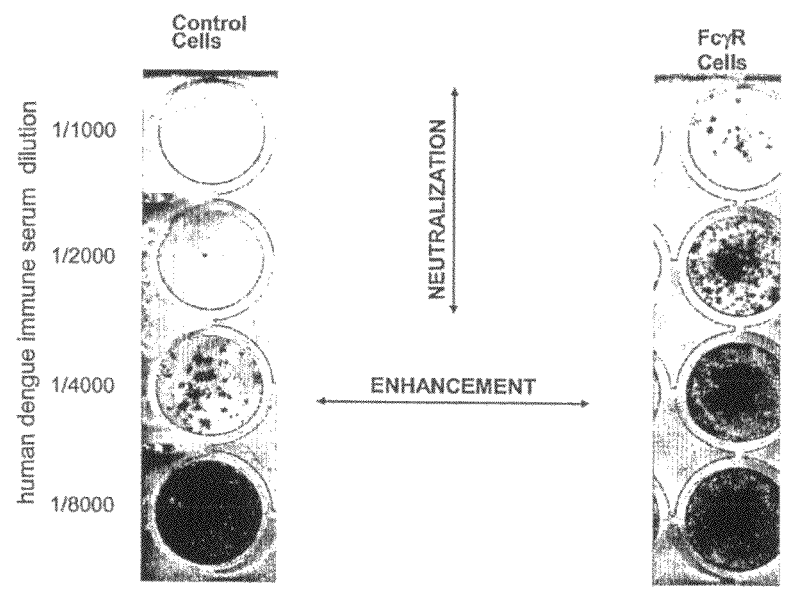
FIG. 3 is an image showing the results of an assay carried out as illustrated in FIGS. 1-2. An increase in plaque formation from one dilution to the next in the FcγR cells indicates that the immune serum does not contain neutralizing antibodies. An increase in plaque formation at each dilution in the FcγR cells relative to the control cells indicates that the immune serum contains immune-enhancing antibodies.

According to one embodiment, illustrated in FIGS. 1-3, a virion-antibody mixture is prepared and virion-antibody complexes are allowed to form. The conditions shown in FIG. 1 are exemplary. Thereafter, the serum containing the virion-antibody complexes is exposed to each of a monolayer of recombinant cells expressing a desired Fc receptor and a monolayer of control cells (preferably mock transfected mammalian cells of the type used to express the recombinant Fc receptor). The exposure process is preferably carried out over multiple dilutions, although the use of multiple dilutions, per se, is not required.

In any event, infectivity is measured using any appropriate protocol for discriminating between infected cells and non-infected cells (described infra). The number of infected cells can be counted and the results of each trial can be compared. By comparing similarly diluted sera, it is possible to determine whether the particular serum tested is capable of affording enhancement of infection in those cells that express the particular Fc receptor. For example, in FIG. 2 enhancement is evident by comparing the infectivity of control cells versus recombinant cells at each of the dilutions tested. The titer of neutralizing antibodies present in the immune serum can also be assessed by measuring the degree of virion neutralization/infectivity at the several dilutions tested.

FIG. 3 illustrates the results obtained using a plaque assay to assess whether a human dengue immune serum could be screened for immune enhancement. The human dengue immune serum-dengue virus mixture was exposed to mock transfected cells (left) and cells expressing a combinant Fcγ receptor (right). The immune serum caused enhancement of infection, which is apparent by comparing plaque formation between cell types at 1/1000, 1/2000, and 1/4000 dilutions.

Figure 4:
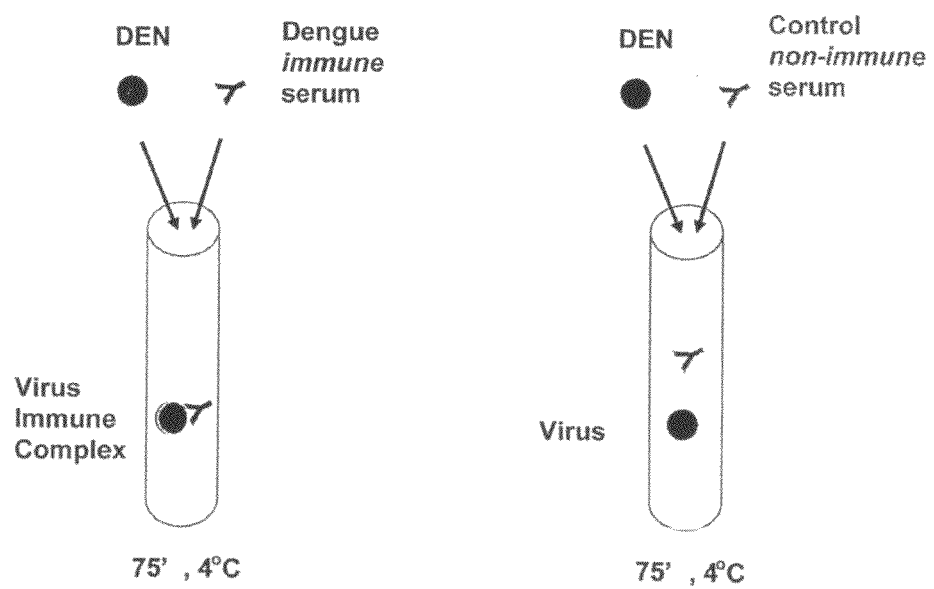
FIG. 4 is a schematic diagram illustrating the formation of virion-antibody mixtures to be used in a representative simultaneous neutralization/enhancement assay of the present invention. Dengue virus virions ("DEN") are exposed to an antiserum containing anti-Dengue virus antibodies to form a virion-antibody mixture containing Dengue virion-antibody complexes (left), and to a control antiserum that does not contain anti-Dengue virus antibodies to form a control virion-antibody mixture that does not contain Dengue virion-antibody complexes (right).
Figure 5:
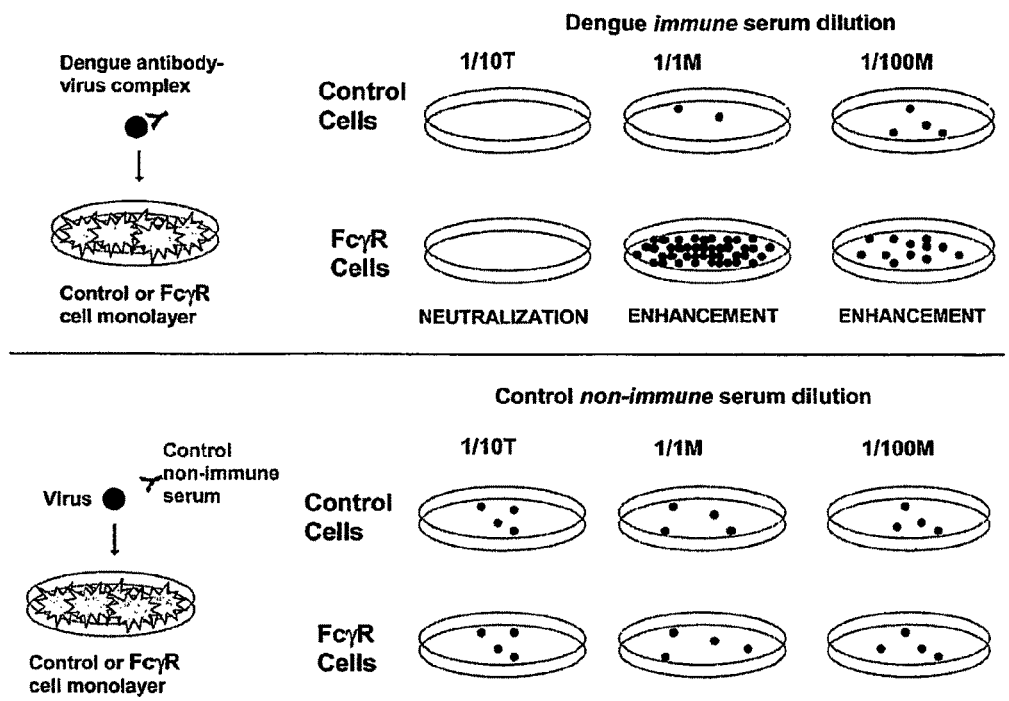
FIG. 5 is a schematic diagram illustrating a representative simultaneous neutralization/enhancement assay of the present invention. Virion-antibody mixtures, formed as illustrated in FIG. 4 by exposing the virions to different dilutions of each antiserum, are contacted with cells expressing a recombinant Fcγ receptor ("FcγR Transfectant") and with control cells that do not express the recombinant receptor, and plaques are allowed to form. Neutralization and enhancement are assessed by comparing the infectivity of the two virion-antibody mixtures in the FcγR-expressing cells at a certain dilution. A decrease in infectivity of the Dengue-immune antiserum relative to infectivity of the non-immune antiserum would indicate that the Dengue-immune antiserum contains neutralizing antibodies. An increase in infectivity of the Dengue-immune antiserum relative to infectivity of the non-immune antiserum would indicate that the Dengue-immune antiserum contains immune-enhancing antibodies.

According to a second embodiment, illustrated in FIGS. 4-5, first and second virion-antibody mixtures are prepared and virion antibody complexes, if any, are allowed to form. The conditions shown in FIG. 4 are exemplary. The first mixture is prepared with an antiserum containing antibodies capable of forming such complexes, whereas the second mixture (a control) is prepared with an antiserum substantially lacking antibodies capable of forming such complexes. Both of the first and second mixtures are then exposed to each of a monolayer of recombinant cells expressing a desired Fc receptor and a monolayer of control cells. The exposure is preferably carried out over multiple dilutions, although as noted above the use of multiple dilutions is not required.

Infectivity is measured and the number of infected cells can be counted. The results of each trial can be compared. By comparing similarly diluted sera, it is possible to determine whether the particular serum tested is capable of affording enhancement of infection in those cells that express the particular Fc receptor. For example, in FIG. 5 enhancement is evident by comparing the infectivity of the control cells exposed to the first mixture (first row) to the infectivity of the FcγR-transfected cells exposed to the first mixture (second row), and/or comparing the infectivity of the FcγR-transfected cells exposed to the first mixture (second row) to the infectivity of the FcγR-transfected cells exposed to the second mixture (fourth row). The titer of neutralizing antibodies present in the immune sera can also be assessed by measuring the degree of virion neutralization/infectivity at several dilutions tested.

Measuring of infectivity may be carried out by any suitable method for measuring viral infectivity, as will be apparent to one of ordinary skill in the art. Suitable methods include detecting the presence of any protein that is absent, or not present in any appreciable amount, in the virion itself, but only produced, or augmented in abundance, upon initiation of infection. Exemplary proteins of this type include nonstructural proteins and/or certain envelope proteins of the virion. To detect dengue virus infectivity, nonstructural protein NS-1 and/or envelope E protein, for example, may be detected using a secondary antibody labeled for detection (enzymatic, fluorochrome, etc.). Detection may be carried out, for example, by enzyme-linked immunosorbent assay and/or flow cytometry.

As noted above, another aspect of the present invention relates to a method of determining both neutralization and immune enhancement of virus infectivity. Basically, each trial is performed in a manner that affords a second infectivity standard. A decrease in infectivity relative to the second infectivity standard indicates that antibodies in the first virion-antibody mixture neutralize virus infectivity.

The second infectivity standard can be a statistically predetermined range of positive infections that one would expect to be measured under a particular experimental protocol. The standard can be set at a 95%, 97%, 98% or 99% confidence level. Alternatively, the infectivity standard can be an internal control performed in parallel with the test assay of the present invention. Basically, a second virion-antibody mixture is exposed to a second set of cells, and infectivity of the second virion-antibody mixture is measured in the second set of cells. Any difference in infectivity between the first and second set of cells can then be compared.

The use of internal controls is described in relation to the embodiments described above. As described in relation to the embodiment illustrated in FIGS. 1-3, by comparing sera of different dilutions, it is possible to determine whether the particular serum tested is capable of neutralizing infection in those cells that express the particular Fc receptor. For example, in FIG. 2 neutralization would be evident by comparing the infectivity of dilution 1/2000 versus dilution 1/1000 in the recombinant cells. A decrease in infectivity in the higher dilution relative to the lower dilution would evidence neutralization. The titer of neutralizing antibodies present in the immune serum can also be assessed by measuring the degree of virion neutralization/infectivity at the several dilutions tested.

According to the second embodiment illustrated in FIGS. 4-5, by comparing similarly diluted sera, it is possible to determine whether the particular serum tested is capable of affording neutralization against infection of those cells that express the particular Fc receptor. For example, in FIG. 5 neutralization is evident by comparing the infectivity of the control cells or the FcγR-transfected cells exposed to the first mixture (first or second row) to the infectivity of the control cells or the FcγR-transfected cells exposed to the second mixture (third or fourth row). The titer of neutralizing antibodies present in the immune sera can also be assessed by measuring the degree of virion neutralization/infectivity at several dilutions tested.

From the foregoing, it should be appreciated that the present invention can be used to screen active vaccines to determine whether those vaccines are likely to induce an immune response that can enhance subsequent infections by a different strain of the same virus or a different virus. Such screening can be a part of a routine procedure implemented prior to beginning or concurrent with human vaccine trials. Screening of vaccines for inoculating non-human mammals, e.g., veterinary vaccines, is also contemplated.

Likewise, the present invention can be used to screen passive vaccines for their ability to cause immune enhancement of infections by any virus.

Further, the present invention can be used to identify any agents (drugs, environmental conditions, etc.) that can modulate the activity of an Fc receptor to exacerbate or inhibit immune enhancement by a particular immune serum/virus.

In addition to the foregoing uses, the present invention can be used to identify/confirm whether a particular virus is capable of inducing an immune response that is likely to cause immune enhancement for subsequent infections by the same virus or a different virus. In this manner, the particular Fc receptor implicated in immune enhancement can also be identified. By using antibodies that bind specifically to a particular virus epitope to form the virion-antibody complexes, the assays of the present invention can also be used to identify a virus epitope implicated in immune enhancement. The antibodies that are specific for an epitope can be in the form of a monoclonal antibody or active fragment thereof, or a substantially monospecific polyclonal antiserum, both of which are described above. The epitopes can be surface-exposed linear epitopes or conformational epitopes, and either neutralizing or non-neutralizing.

As noted above, the recombinant Fc receptor can be signaling competent or signaling incompetent. According to another embodiment, the infectivity of a virus can be compared between a recombinant cell expressing a signaling-competent Fc receptor and a recombinant cell expressing a signaling-incompetent Fc receptor (along with any other controls). In this manner, agents that may block or interfere with signaling-dependent immune enhancement can be screened by exposing the cells with the signaling-competent Fc receptor to the agent. Substantially the same infectivity between the two groups of cells (signaling-competent Fc receptor+agent versus signaling-incompetent Fc receptor) indicates that the agent decreases intracellular signaling of the receptor.

In contrast, where the agent increases infectivity of the signaling-competent Fc receptor cells relative to untreated/unexposed cells of the same type, an assessment can be made as to whether the agent enhances signaling-dependent infectivity of a particular Fc receptor.

The recombinant cells of the present invention are prepared by transfecting a mammalian cell with one or more DNA constructs encoding an Fc receptor and any accessory proteins (required for Fc receptor binding, uptake, or signaling). The cells can either be transiently transfected or stably transfected, the latter being preferred. The DNA construct is preferably in an expression vector that affords stable integration.

At a minimum, the DNA constructs used to recombinantly express a particular Fc receptor include appropriate 5' and 3' regulatory sequences ligated to a nucleic acid molecule encoding a desired Fc receptor. Any suitable 5' and 3' regulatory regions can be utilized in preparing the recombinant cells. Preferred promoters are either constitutive or inducible. Promoters and transcription terminal signals that are active in mammalian cells are well known to those of skill in the art of molecular biology.

According to one embodiment, the DNA construct includes a first DNA molecule that encodes an Fc receptor γ-chain polypeptide and a second DNA molecule that encodes an Fc receptor α-subunit. The first DNA molecule is preferably located upstream of the second DNA molecule. Exemplary Fc receptors include, without limitation, the γ-chain and α-subunits of FcγRIA, FcRIIIA, FcεRI, and FcαRI (Daëron, M., "Fc Receptor Biology," *Annu Rev Immunol* 15:203-34 (1997), which is hereby incorporated by reference in its entirety).

The DNA construct of this embodiment may further include an internal ribosomal entry site located between the first and second DNA molecules, and/or a promoter operably coupled to the first and second DNA molecules wherein the promoter is located 5' of the first DNA molecule and the first DNA molecule is located 5' of the second DNA molecule.

In a preferred embodiment, the second DNA molecule includes a nucleic acid that encodes a FcγRIA α-subunit (CD64) and the first DNA molecule includes a nucleic acid that encodes the FcγRIA γ-chain. Bicistronic expression vectors of this type are described in Examples 3 and 9, infra.

The present invention further relates to one or more recombinant cell types or stably transfected cell lines that can be used in a screening assay of the present invention. These cell types or cell lines include, without limitation, a cell that expresses an Fc receptor competent for binding and uptake of virion-antibody complexes; and a cell that expresses an Fc receptor competent for binding and uptake of virion-antibody complexes but not for signaling. Preferably, the Fc receptor is expressed in a density substantially similar to the density present in native monocytes and/or macrophages.

Additional aspects of the present invention relate to kits for performing any method of the present invention. The kits can include any one or more cells or cell lines of the present invention, any one or more control cells, as well as (optionally) cell culture media, vessels for culturing the various cells, suitable detecting antibodies that can be used to measure infectivity (as described above), and instructions for carrying out the assays of the present invention.

EXAMPLES

The following examples are intended to illustrate, but by no means are intended to limit, the scope of the present invention as set forth in the appended claims.

Example 1

Cells and Dengue Viruses

COS-7 fibroblasts and Vero cells were grown in Dulbecco's Modified Eagle Medium (DMEM) or Minimal Essential Medium (MEM), respectively. THP-1 cells, kindly provided by Dr. Melanie Wellington (University of Rochester, Rochester N.Y.), were grown in RPMI medium in stationary culture. C6/36 *Aedes albopictus* mosquito cells were grown at 28° C. in MEM supplemented with sodium pyruvate and non-essential amino acids. Media were supplemented with fetal bovine serum and cells were grown in a 5% $CO_2$ atmosphere. Virulent strain 16681 dengue 2 virus (Halstead & Simasthien, "Observations Related to the Pathogenesis of Dengue Hemorrhagic Fever. II. Antigenic and Biologic Properties of Dengue Viruses and Their Association with Disease Response in the Host," *Yale J Biol Med* 42(5):276-92 (1970), which is hereby incorporated by reference in its entirety), and strain New Guinea C (NGC) dengue 2 virus, attenuated by multiple passage in suckling mouse brain (Sabin, "Research on Dengue During World War II," *Am. Trop. Med. Hyg.* 1(1): 30-50 (1952), which is hereby incorporated by reference in its entirety), were gifts of Drs. Walter Brandt (Walter Reed Army Institute of Research, Washington, D.C.) and Tadeusz Kochel (U.S. Naval Medical Research Center, Bethesda, Md.). Each virus was propagated in mosquito cells and titered by plaque assay in Vero cells.

Example 2

Dengue Antibodies

Convalescent anti-dengue sera from That or Puerto Rican dengue fever patients (gifts from Drs. Eric Henchal (Armed Forces Institute for Medical Research, Bangkok, Thailand) and Gladys Sather (Centers for Disease Control, Puerto Rico), respectively) were pooled using equal amounts from each of six subjects; the pool exhibited broad dengue serotype neutralizing and hemagglutination-inhibiting activity. An IgG1 mouse monoclonal antibody against dengue 2 NS1 (Mab 9A9) was used to detect dengue virus replication in plaque assays.

Example 3

Figure 6:
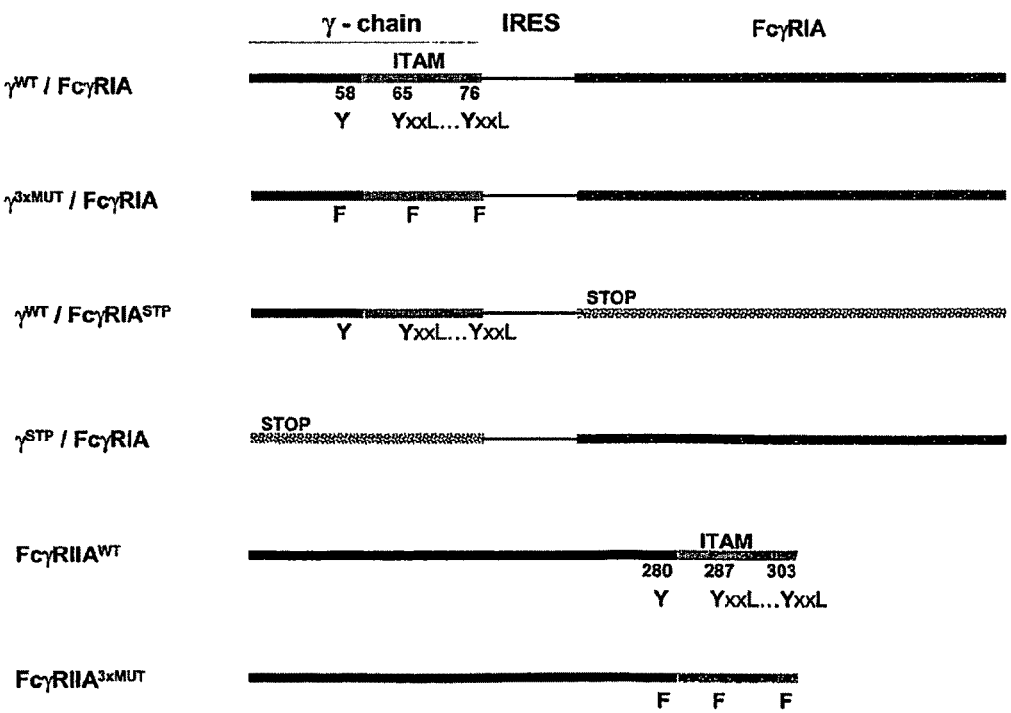
FIG. 6 is a diagram showing the structure of γ-chain/FcγRIA complex and FcγRIIA versions used in COS transfectants. The order of γ-chain and FcγRIA genes in the bicistronic construct assured that FcγRIA-expressing COS cells also expressed the γ-chain ($\gamma^{WT}$/FcγRIA). An encephalomyocarditis virus-derived internal ribosomal entry site (IRES) drives internal initiation of the FcγRIA gene. Other genes are expressed under the control of a Cytomegalovirus Immediate Early (CMV IE) promoter. Stop codons inserted into the FcγRIA or $\gamma^{WT}$-chain sequence of bicistronic constructs provided control vectors. FcγRIIA was cloned into the same pcDNA5/FRT to generate a monocistronic construct (FcγRIA$^{WT}$; FcγRIIA$^{3\times MUT}$). A concensus Kozak sequence was introduced upstream of the γ-chain and FcγRIIA genes. Tyrosine residue positions in immunoreceptor tyrosine activation motifs (ITAM) of γ-chain and FcγRIIA are numbered starting from +1 start.

Construction of Signaling-Competent and Signaling-Incompetent γ-Chain/FcγRIA or FcγRIIA Vectors Human FcγRIA (Fanger et al., "Type I (CD64) and Type II (CD32) Fcγ Receptor-mediated Phagocytosis by Human Blood Dendritic Cells," *J Immunol* 157(2):541-8 (1996), which is hereby incorporated by reference in its entirety) and γ-chain (Katsumata et al., "Association of FcγRII with Low-density Detergent-resistant Membranes is Important for Cross-linking-dependent Initiation of the Tyrosine Phosphorylation Pathway and Superoxide Generation," *J Immunol* 167(10):5814-23 (2001), which is hereby incorporated by reference in its entirety) cDNA were generously provided by Drs. Clark L. Anderson (Ohio State University, Columbus Ohio) and Jean-Pierre Kinet (Harvard University, Cambridge Mass.), respectively. FcγRIIA, H131 allotype (Takai, T., "Roles of Fc Receptors in Autoimmunity," *Nat Rev Immunol* 2(8):580-92 (2002), which is hereby incorporated by reference in its entirety) was provided by Dr. Jan G. J. van de Winkle (University Hospital Utrecht). To arrange for coordinated expression of FcγRIA with γ chain, a polymerase chain reaction (PCR)-based strategy was used to construct a bicistronic expression cassette in a pcDNA5/FRT backbone that contained the coding sequences of γ chain and FcγRIA in the upstream and downstream positions, respectively, separated by an internal ribosomal entry site (IRES) derived from encephalomyocarditis virus (ECMV), and expressed under the control of the Cytomegalovirus Immediate Early (CMV IE) promoter. Control constructs were generated by site-directed mutagenesis using standard methods (Quikchange II, Stratagene, La Jolla, Calif.) to insert stop codons within γ chain or FcγRIA. Similar methods were used to generate constructs that contained single, double, or triple ITAM tyrosine residue mutations in multiple permutations. FcγRIIA was also generated in the pcDNA5/FRT backbone in monocistronic form. Sequences of all constructs were verified by DNA sequence analysis. Cloning was followed by propagation in JM109 *E. coli* and purification by Qiagen affinity columns. These constructs are illustrated in FIG. 6.

Example 4

Transient Fcγ Receptor Expression in COS Cells

Purified recombinant plasmids were transfected into COS cell monolayers using standard methods (Lipofectamine 2000, Invitrogen, Carlsbad, Calif.). Cell cultures were trypsinized 48 hours after transfection, washed with PBS, and kept on ice for immediate use. FcγR expression was verified by rosette assay using sheep red blood cells (SRBC) opsonized with rabbit IgG anti-SRBC. The percentage of cells expressing FcγR was assessed by counting SRBC rosettes in a hemacytometer and by flow cytometry. FcγRIA/γ-chain genetic sequences were confirmed by DNA sequence analysis following cloning of each construct into the pcDNA5/FRT vector. Plasmid expression constructs were propagated in *E. coli* and purified using standard methods. γ-Chain expression in transiently transfected COS-7 lines was demonstrated by immunoprecipitation and Western blot using anti-γ chain rabbit antiserum. Frequencies of FcγR-expressing cells and density of surface expression among transient transfectants were measured by flow cytometry using FcγRI (CD64) phycoerythrin-labeled monoclonal antibodies. The efficiency of transfection among constructs varied from one experiment to another, but differences generally were less than 20% among transient transfectants dually expressing FcγRIA and γ-chain versions; transfection efficiency was uniformly lowest with the IRES-CD64 construct. The density of FcγRIA expression, however, was comparable among the COS-7 transfectants that expressed the receptor.

Example 5

Flow Cytometry

THP-1 cells and COS transfectants were washed with PBS and stained with R-Phycoerythrin-conjugated IgG1 monoclonal antibodies against human FcγRIA (CD64 Mab 10.1; eBiosciences, San Diego, Calif.) or FcγRIIA (CD32 Mab AT10; Serotec, Raleigh, N.C.) using an R-PE-labeled IgG1 isotype control from the corresponding manufacturer. Stained cells were fixed with 1% paraformaldehyde and analysed by FACSCalibur using CellQuest software (BD Immunocytometry Systems, Franklin Lakes, N.J.); a minimum of 20,000 events were collected from each sample for analysis. The number of FcγRIA or FcγRIIA molecules expressed on the surface of COS transfectants and THP-1 cells was determined by a quantitative immunofluorescence method that employed standardized QuantiBRITE-PE beads (BD Pharmingen, San Jose, Calif.) following the manufacturer's instructions. Briefly, the fluorescent intensity of PE-labeled beads was used to establish a standard curve. The number of cell surface FcγRIA and/or FcγRIIA molecules per cell was then extrapolated from the standard after subtracting background staining of the IgG1 isotype control.

Example 6

Western Blotting

COS cell transfectants were lysed in TRIS saline buffer containing 1% NP-40 and protease inhibitors. Soluble proteins were reduced in Laemmli buffer and separated by 15% SDS-polyacrylamide gel electrophoresis for transfer to nitrocellulose membranes and immunoblotting with rabbit IgG anti-human γ-chain (Upstate Cell Signaling Solutions, Lake Placid, N.Y.) and chemiluminescence-based detection (ECL Amersham Biosciences, Piscataway, N.J.). γ-Chain abundance was quantified by gel-scanning densitometry using ImageQuant version 5.2 software (Molecular Dynamics).

Example 7

Measurement of Opsonized Particle Binding and Phagocytosis

Sheep red blood cells were sensitized with a subagglutinating dilution of rabbit IgG anti-sheep RBC and incubated with transfected COS cells in suspension for 18 hours at room temperature before counting in a hemocytometer chamber; SRBC rosettes were expressed as the percentage of cells with at least 3 SRBC bound. Surface binding and phagocytosis of opsonized *Candida albicans* were determined by a previously described quantitative double fluorescence method (Wellington et al., "Enhanced Phagocytosis of *Candida* Species Mediated by Opsonization with a Recombinant Human Antibody Single-chain Variable Fragment," *Infect Immun* 71(12):7228-31 (2003), which is hereby incorporated by reference in its entirety). Briefly, heat-killed yeast cells were stained with FITC and sensitized with rabbit antiserum. To measure phagocytosis, transfected COS cells were incubated with opsonized FITC-labeled yeast particles for 45 minutes at 4° C. followed by incubation for 45 minutes at 37° C. before counterstaining with ethidium bromide. In parallel, mixtures of COS transfectants and yeast particles were incubated at 4° C. to determine cell surface binding. Cell surface-bound yeast particles were counterstained yellow by ethidium bromide, but internalized FITC-stained yeast particles continued to fluoresce green since ethidium bromide cannot penetrate viable cells. Phagocytic activity of COS transfectants and THP-1 cells was expressed as the phagocytic index, the number of opsonized yeast particles ingested per 100 FcγR-expressing cells. Cell preparations were photographed at 40× with an Olympus BX41TF fluorescent microscope equipped with a digital camera using Qcapture 2.0 software. Images were prepared in Adobe Photoshop CS.

Example 8

Measurement of Dengue 2 Virus Replication by Plaque Assay

Pre-formed dengue immune complexes were prepared by incubating mixtures of serially diluted virus or human pooled dengue antibody, in checkerboard fashion, for 75 minutes at 37° C. before mixing with $2\times10^5$ trypsinized COS transfectants suspended in 24-well polystyrene cluster plates. After overnight incubation at 37° C., cell monolayers were washed with PBS and overlaid with 0.6% agarose (SeaKem GTG, FMC BioProducts, Rockland, Me.). Agarose plugs were removed three days later and cells were fixed with an acetone-methanol mixture. Dengue plaques developed with anti-dengue 2 NS1 Mab and a Nickel-HRP-based detection method (Vectastain ABC kit, Vector Laboratories, Burlingame, Calif.) were counted with the aid of a 10× magnifying glass or by scanning the cluster plate into Adobe Photoshop CS for further magnification.

Example 9

Figure 7:
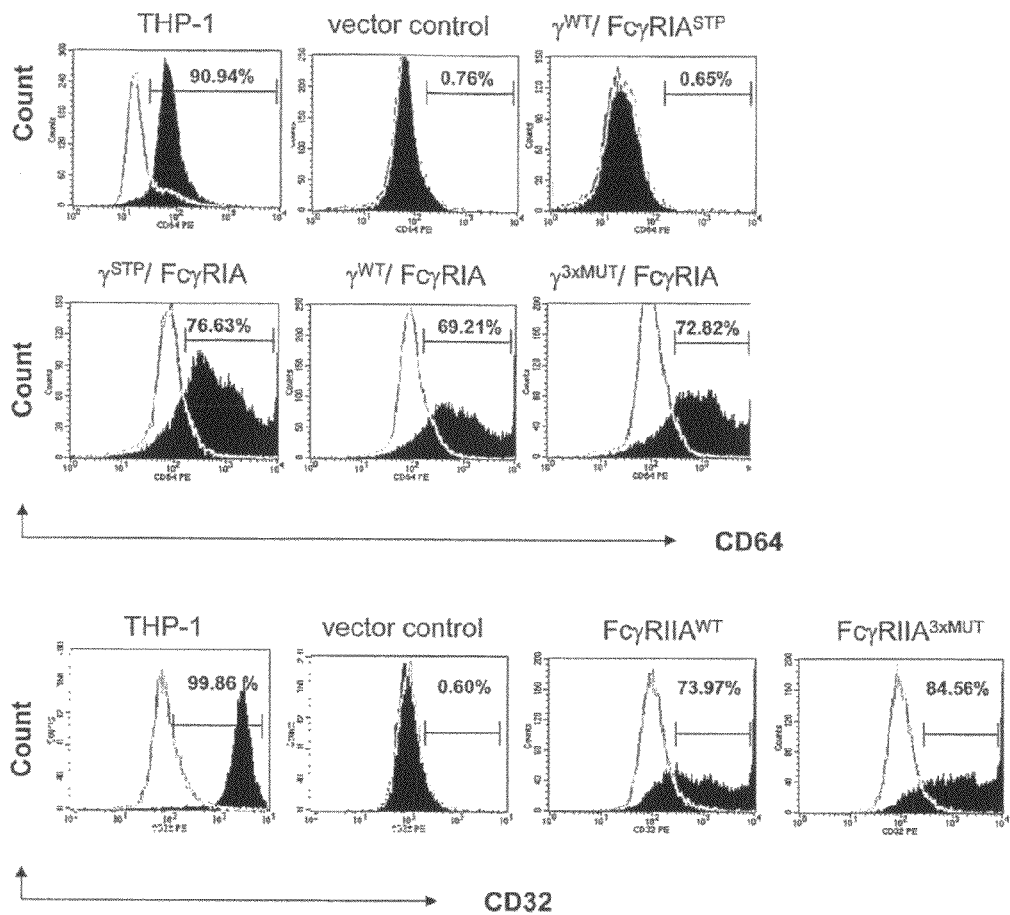
FIG. 7 is a series of histograms of FcγRIA (CD64) (top) and FcγRIIA (CD32) (bottom) expression levels in COS transfectants and a THP-1 control cell. Phycoerythrin (PE)-labeled CD32 (Mab AT10) or CD64 (Mab 10.1) monoclonal antibodies and PE-labeled mouse IgG1 were used to measure the proportion of COS transfectants expressing the respective FcγR. The THP-1 human macrophage cell line served as a control. Results are representative of 5 to 6 determinations for FcγRIA transfectants and 3 determinations for FcγRIIA transfectants (see Table 1).
Figure 8:
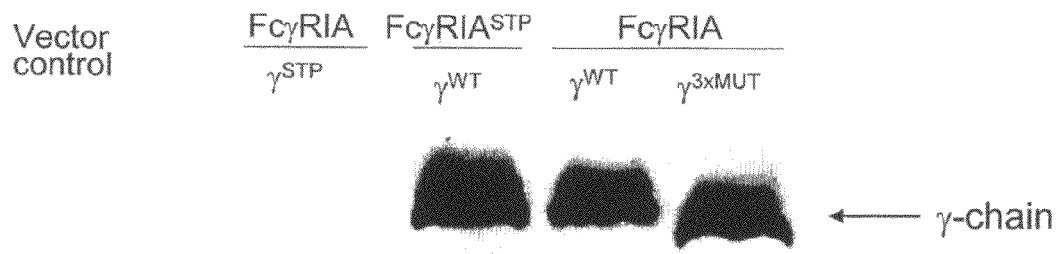
FIG. 8 is a Western blot verifying γ-chain expression. Solubilized lysates prepared from $2.5 \times 10^5$ cells of each COS transfectant were electrophoresed and subjected to Western blot using a monospecific rabbit serum against human γ-chain (Letourneur et al., "Characterization of the Family of Dimers Associated with Fc Receptors (FcεRI and FcγRIII)," *J Immunol* 147(8):2652-6 (1991), which is hereby incorporated by reference in its entirety).

Signaling-Competent and Signaling-Incompetent FcγRIA and FcγRIIA Expressed in COS Cells FcγRIIA exists in two functionally different allelic forms that are determined by a single His/Arg residue at position 131 (Warmerdam et al., "Polymorphism of the Human Fcγ Receptor II (CD32): Molecular Basis and Functional Aspects," *Immunobiol* 185(2-4):175-82 (1992), which is hereby incorporated by reference in its entirety); the H131 form was selected for the present studies because it, unlike the R131 form, efficiently binds IgG2 in addition to the other human IgG subclasses. The sequence of each gene construct was verified by comparing with that published in GenBank. γ/FcγRIA and FcγRIIA gene constructs used in these experiments are presented in FIG. 6. Earlier investigations that defined a γ-chain signaling requirement for FcγRIA-mediated phagocytosis by COS transfectants have employed separate vectors or FcγRIA-γ-chain chimeras to express these genes (Kim et al., "Fcγ Receptor Transmembrane Domains: Role in Cell Surface Expression, γ Chain Interaction, and Phagocytosis," *Blood* 101(11):4479-84 (2003); Lowry et al., "Functional Separation of Pseudopod Extension and Particle Internalization During Fcγ Receptor-mediated Phagocytosis," *J Exp Med* 187(2):161-76 (1998), which are hereby incorporated by reference in their entirety). To assure stoichiometrically uniform FcγRIA and γ-chain co-expression in transfected cells, the respective genes were incorporated into a bicistronic vector with γ-chain being inserted upstream of FcγRIA so that FcγRIA transfectants detected by rosette formation with opsonized particles or by flow cytometry using anti-CD64 monoclonal antibodies were also assured to contain γ-chain. This gene arrangement would be predicted to result in expression of γ-chain in excess of FcγRIA (roughly by a factor of two), presumably due to the inherent inefficiency of ribosomal entry (Hennecke et al., "Composition and Arrangement of Genes Define the Strength of IRES-driven Translation in Bicistronic mRNAs," *Nucleic Acids Res* 29(16):3327-34 (2001); Martinez-Salas, E., "Internal Ribosome Entry Site Biology and its Use in Expression Vectors," *Curr Opin Biotechnol* 10(5):458-64 (1999), which are hereby incorporated by reference in their entirety). A stoichiometric γ-chain excess was desired, since each transmembrane FcγRIA monomer associates with a γ-chain dimer to form the functional complex. It also served to increase the likelihood that cells exhibiting surface expression of FcγRIA by flow cytometry would also likely contain γ chain, which is largely intracellular and therefore cannot be detected by this method without permeabilization. Stop codons were inserted into the FcγRIA or $\gamma^{WT}$-chain sequence of bicistronic constructs (see FIG. 1) to provide control vectors. The γ-chain cytoplasmic tail incorporates three tyrosine residues: one (Y58) upstream of the ITAM, and two ITAM tyrosine residues (Y65 and Y76). An analogous tyrosine residue distribution (upstream Y280; ITAM Y287, Y303) obtains for the FcγRIIA cytoplasmic tail where earlier molecular dissection of phagocytosis-related signaling indicated that the upstream non-ITAM tyrosine residue also contributed to this function (Indik et al., "The Molecular Dissection of Fcγ Receptor Mediated Phagocytosis," *Blood* 86(12):4389-99 (1995); Kim et al., "Fcγ Receptors Differ in Their Structural Requirements for Interaction with the Tyrosine Kinase Syk in the Initial Steps of Signaling for Phagocytosis," *Clin Immunol* 98(1):125-32 (2001); Mitchell et al., "Substitutions and Deletions in the Cytoplasmic Domain of the Phagocytic Receptor FcγRIIA: Effect on Receptor Tyrosine Phosphorylation and Phagocytosis," *Blood* 84(6):1753-9 (1994), which are hereby incorporated by reference in their entirety). To assure abrogation of signaling competency of the γ-chain/FcγRIA and FcγRIIA constructs, the three potentially activating tyrosine residues of each receptor were mutated ($\gamma^{3\times MUT}$/FcγRIA; FcγRIIA$^{3\times MUT}$). Flow cytometry was used to verify and to measure FcγR expression, and to determine the number of FcγR molecules on the cell surface. THP-1 cells, a human monocyte line that constitutively expresses FcγRIA and FcγRIIA exclusively (Fleit & Kobasiuk, "The Human Monocyte-like Cell Line THP-1 Expresses FcγRI and FcγRII," *J Leukoc Biol* 49(6):556-65 (1991), which is hereby incorporated by reference in its entirety), was used as a control. The results are shown in FIG. 7 and Table 1. γ-Chain expression was assessed by Western blot, as shown in FIG. 8; equivalence of γ-chain abundance among the γ-chain transfectants was confirmed by scanning densitometry. The percentages of FcγRIA and FcγRIIA-expressing COS cells were comparable among the panel of transfectants (see Table 1) and were at least two to three-fold higher than those previously obtained using a diethylaminoethyl-dextran transfection method (Lowry et al., "Functional Separation of Pseudopod Extension and Particle Internalization During Fcγ Receptor-mediated Phagocytosis," *J Exp Med* 187(2):161-76 (1998); Schlesinger & Chapman, "Influence of the Human High-affinity IgG Receptor FcγRI (CD64) on Residual Infectivity of Neutralized Dengue Virus," *Virology* 260(1):84-8 (1999), which are hereby incorporated by reference in their entirety). THP-1 cells expressed ~5,500 FcγRIA and ~58,000 FcγRIIA surface molecules per cell, amounts that are in agreement with published data (Fleit & Kobasiuk, "The Human Monocyte-like Cell Line THP-1 Expresses FcγRI and FcγRII," *J Leukoc Biol* 49(6):556-65 (1991), which is hereby incorporated by reference in its entirety). The number of FcγRIA or FcγRIIA expressed on COS cells was not affected by Tyr-to-Phe mutations in the associated γ-chain or FcγRIIA cytoplasmic tails, respectively: the average number of cell surface FcγRIIA molecules (~43,000) was greater than that of FcγRIA associated with γ-chain (~30,000), but this difference was not statistically significant (P>0.10; two-tailed t-test). Remarkably, the number of surface FcγRIA molecules was ~50% higher (p<0.03; two-tailed t-test) when this receptor was associated with γ-chain than when it was expressed without it.

TABLE 1

Expression of Human FcγRIA (CD64) and FcγRIIA (CD32) in COS-7 Cells Analyzed by Flow Cytometry

| FcγR | % positive cells (mean ± s.d.) | No. molecules/cell (mean ± s.d.) | (n) |
| --- | --- | --- | --- |
| CD64 | | | |
| THP-1 | 94 ± 4 | 5,487 ± 3,840 | 9 |
| vector control | 0 | 0 | 7 |
| $\gamma^{WT}$ | 0 | 0 | 3 |
| FcγRIA | 75 ± 5 | 17,031 ± 5,771$^a$ | 5 |
| $\gamma^{WT}$/FcγRIA | 79 ± 6 | 28,453 ± 8,530 | 6 |
| $\gamma^{3\times MUT}$/FcγRIA | 84 ± 5 | 31,227 ± 10,872 | 6 |
| CD32 | | | |
| THP-1 | 94 ± 4 | 57,644 ± 9610 | 3 |
| vector control | 0 | 0 | 3 |
| FcγRIIA$^{WT}$ | 59 ± 12 | 41,435 ± 8138 | 3 |
| FcγRIIA$^{3\times MUT}$ | 66 ± 13 | 44,561 ± 8389$^b$ | 3 |

$^a$p < 0.03, FcγRIA vs. $\gamma^{WT}$/FcγRIA or $\gamma^{3\times MUT}$/FcγRIA
$^b$p > 0.10, FcγRIIA vs. $\gamma^{WT}$/FcγRIA or $\gamma^{3\times MUT}$/FcγRIA Example 10

Figure 9A:
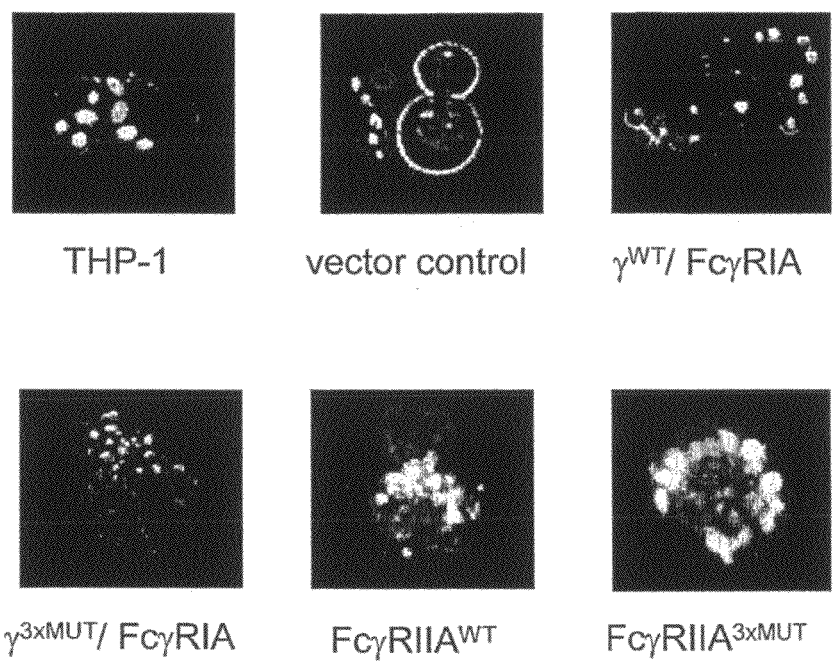
FIGS. 9A-B are a series of images (FIG. 9A) and a graph (FIG. 9B) relating to binding and phagocytosis of opsonized *C. albicans* by COS cells expressing FcγRIA or FcγRIIA. Rabbit IgG-sensitized FITC-stained yeast particles were incubated with COS cells expressing signal-competent ($\gamma^{WT}$/FcγRIA; FcγRIIA$^{WT}$) or signal-incompetent ($\gamma^{3\times MUT}$/FcγRIA; $\gamma^{STP}$/FcγRIA; FcγRIIA$^{3\times MUT}$) FcγR. COS cells expressing γ-chain only or transfected with the pcDNA5/FRT vector served as controls. Phagocytosis by human macrophage-like THP-1 cells that express both FcγR was measured in parallel in each experiment. Binding and phagocytosis of opsonized *C. albicans* was measured using a quantitative double-fluorescence technique that employed ethidium bromide to selectively stain cell-bound but not internalized FITC-stained yeast particles (see Example 10). Immunofluorescent photomicrographs (40×) of FcγR and control cells incubated with opsonized yeast particles are shown in FIG. 9A.
Figure 9B:
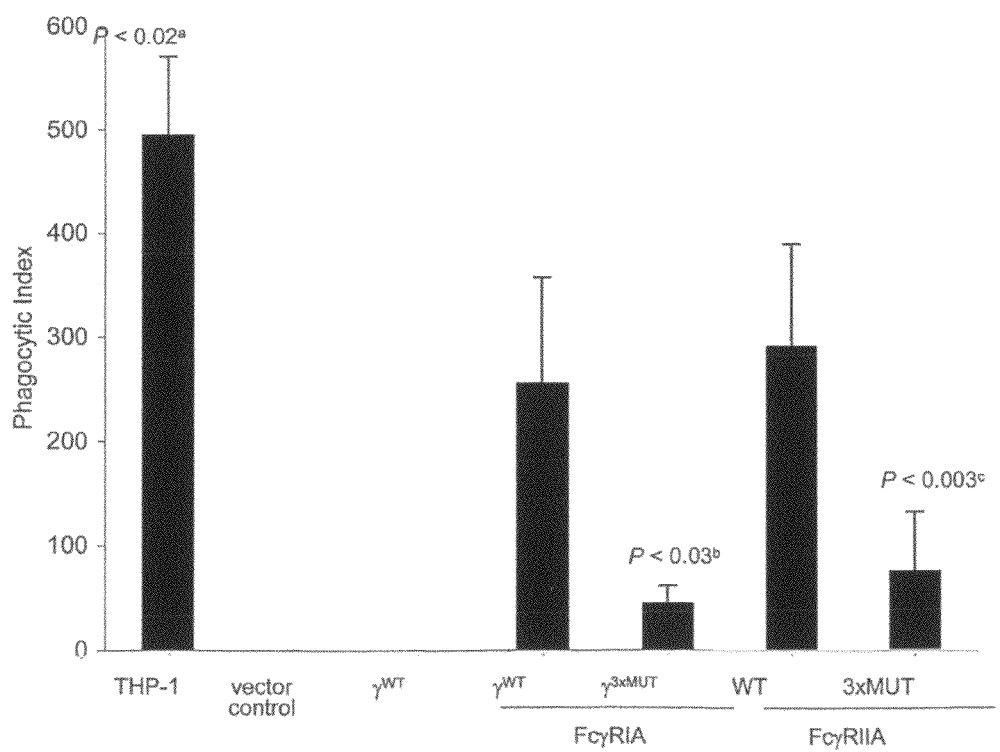

FcγR Surface Expression and Signaling Competency Verified by Binding and Phagocytosis of Opsonized Yeast Particles Signaling-incompetent FcγRIA or FcγRIIA-transfected COS cells bind opsonized SRBC, but are not phagocytic (Kim et al., "Fcγ Receptor Transmembrane Domains Role in Cell Surface Expression, γ Chain Interaction, and Phagocytosis," *Blood* 101(11):4479-84 (2003); Lowry et al., "Functional Separation of Pseudopod Extension and Particle Internalization During Fcγ Receptor-mediated Phagocytosis," *J Exp Med* 187(2):161-76 (1998); Van den Herik-Oudijk et al., "Identification of Signaling Motifs within Human FcγRIIa and FcγRIIb Isoforms," *Blood* 85(8):2202-11 (1995), which are hereby incorporated by reference in their entirety). If properly constructed, the $\gamma^{WT}$/FcγRIA and FcγRIIA$^{WT}$ transfectants were expected to perform both functions, whereas transfectants appropriately mutated or expressing FcγRIA without γ-chain were expected only to bind IgG-coated particles. Binding and phagocytosis of IgG-opsonized yeast particles by COS cells that expressed FcγRIA or FcγRIIA were measured to verify receptor functional activity, and phagocytic THP-1 cells were used as a control. Fluorescence microscopy has been validated as an accurate method to estimate phagocytosis (Lowry et al., "Functional Separation of Pseudopod Extension and Particle Internalization During Fcγ Receptor-mediated Phagocytosis," *J Exp Med* 187(2):161-76 (1998), which is hereby incorporated by reference in its entirety). To simultaneously measure FcγR-mediated binding and phagocytosis, a quantitative double fluorescence method that employed IgG-opsonized FITC-stained *C. albicans* particles and ethidium bromide counterstaining was adopted to distinguish between THP-1 cell surface bound and internalized particles (Wellington et al., "Enhanced Phagocytosis of *Candida* Species Mediated by Opsonization with a Recombinant Human Antibody Single-chain Variable Fragment," *Infect Immun* 71(12):7228-31 (2003), which is hereby incorporated by reference in its entirety). FIG. 9A illustrates the appearance of surface-bound or internalized fluorescent-stained yeast particles after incubation with THP-1 cells or COS cells that expressed γ/FcγRIA or FcγRIIA. COS cells transfected with the control empty vector or $\gamma^{WT}$/FcγRIA$^{STP}$ did not bind opsonized particles. In accord with receptor expression measured by flow cytometry (see Table 1), more THP-1 cells (~90%) bound opsonized yeast particles than did the FcγR transfectants, where the levels were similar (50-60%). Comparable results were obtained with opsonized SRBC. COS cells expressing FcγR versions that were predicted to be signaling-competent ($\gamma^{WT}$/FcγRIA; FcγRIIA$^{WT}$) exhibited significantly greater phagocytic capacity than did cells expressing the respective signaling-incompetent versions ($\gamma^{3\times MUT}$/FcγRIA, $\gamma^{STP}$/FcγRIA or FcγRIIA$^{3\times MUT}$), as shown in FIG. 9B.

Collectively, these results indicate that the FcγR and γ-chain genes of interest were properly constructed, correctly expressed, and were functional with respect to binding and internalization of IgG-opsonized particles. Having confirmed that these properties of a macrophage were conferred on COS cells, their interaction with dengue immune complexes was investigated as described in Examples 11-12.

Example 11

Figure 10A:
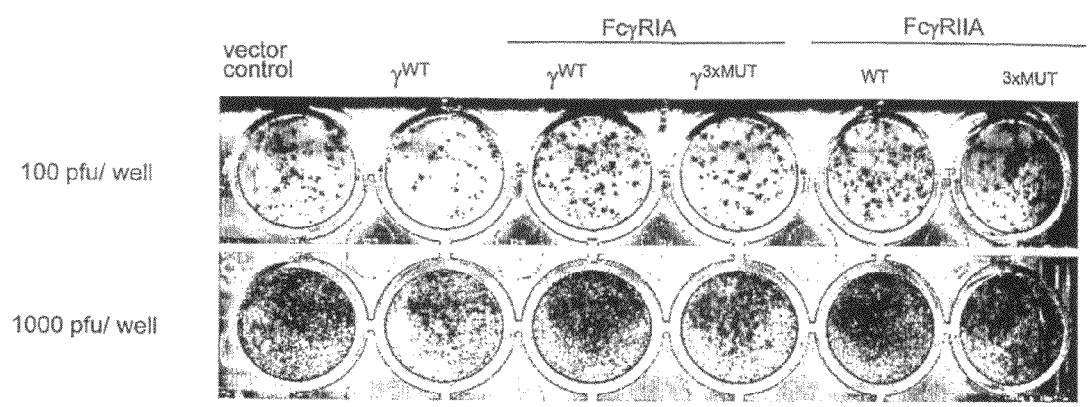
FIGS. 10A-C are images of dengue virus plaques demonstrating that infectivity of virulent strain 16681 or attenuated strain New Guinea C dengue 2 immune complexes is enhanced in COS cells that express FcγRIA or FcγRIIA. The COS transfectants shown in FIG. 10A were infected with 100 or 1,000 PFU dengue 2 (16681) virus in the absence of antibody.
Figure 10B:
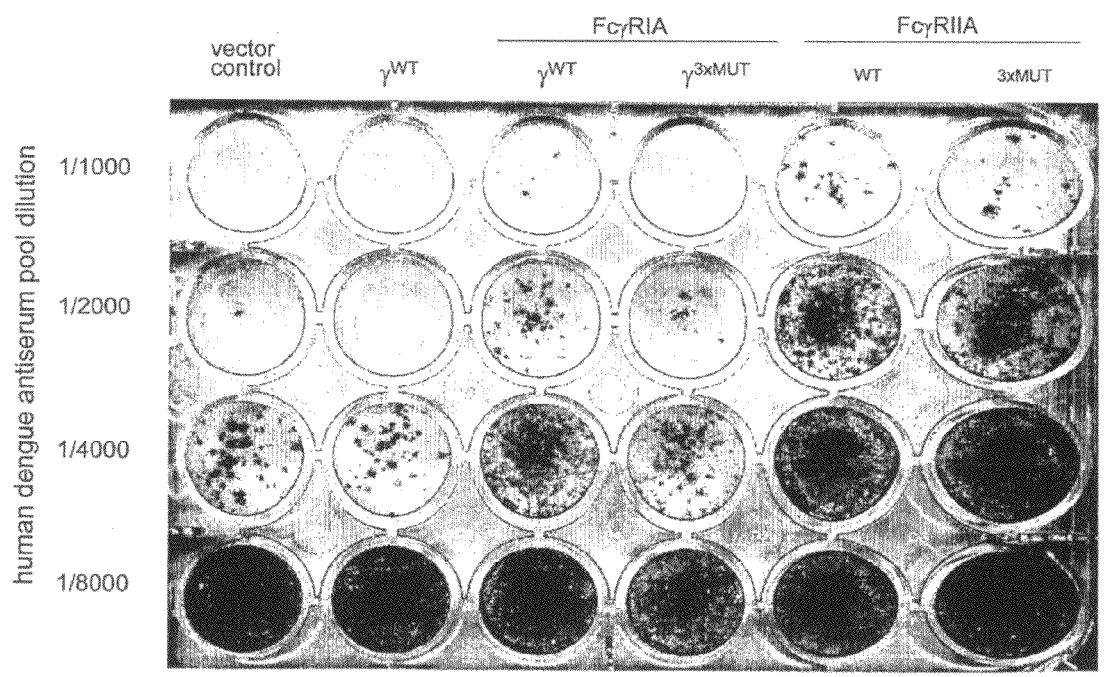
Figure 10C:
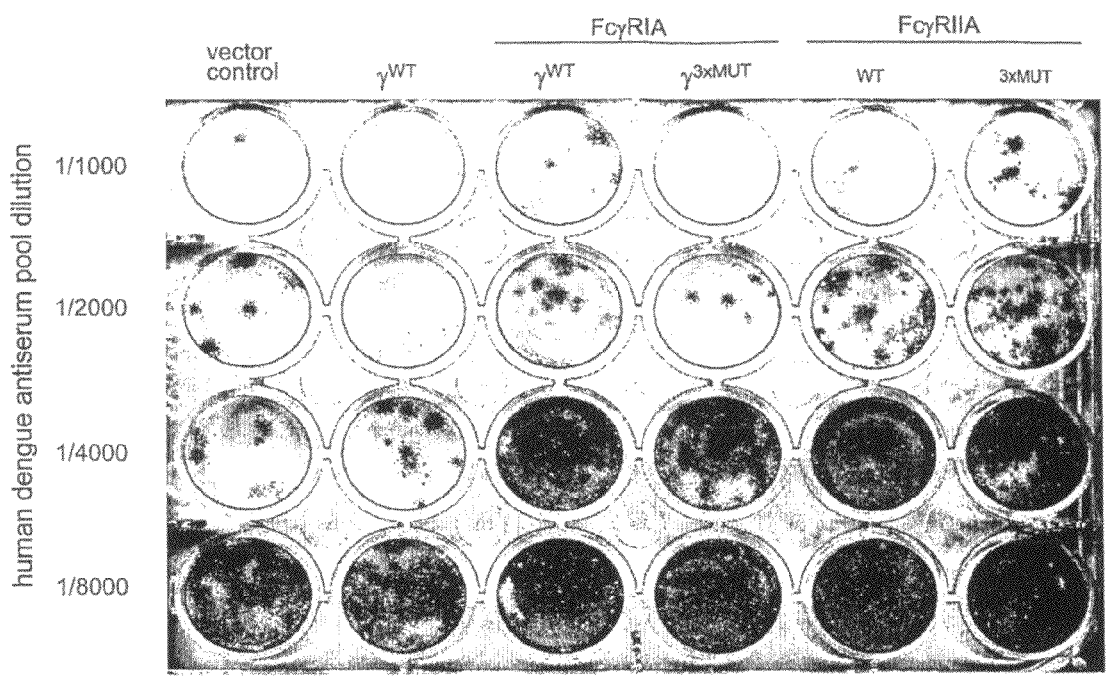
Figure 11A:
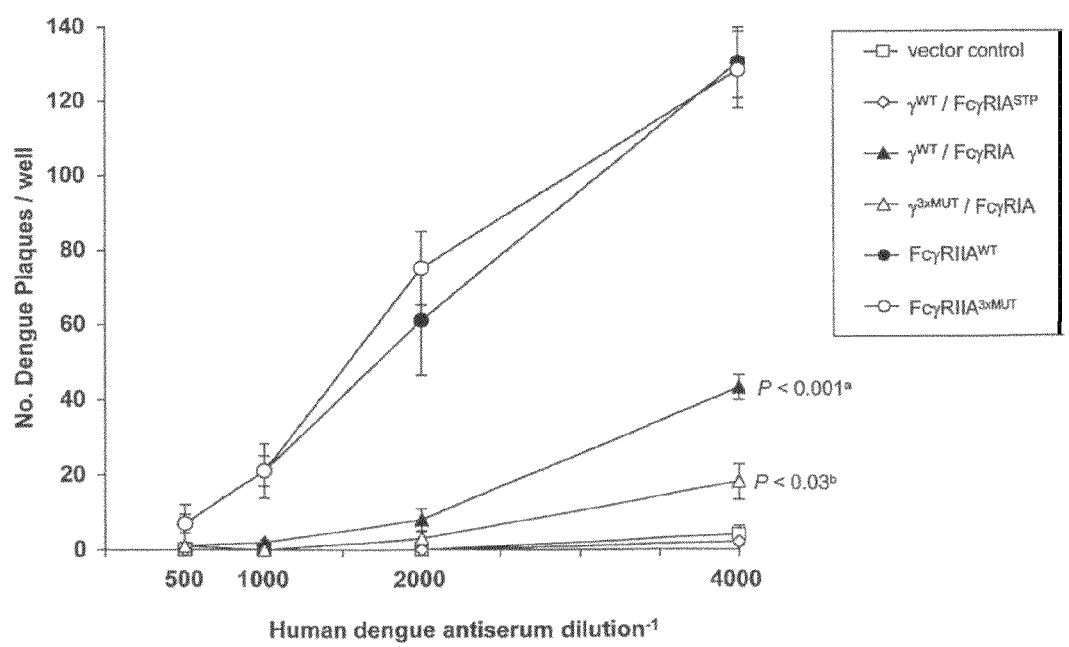
FIGS. 11A-B are graphs showing that signaling-competency is required for optimally enhanced dengue 2 immune complex infectivity mediated by FcγRIA, but not by FcγRIIA.
Figure 11B:
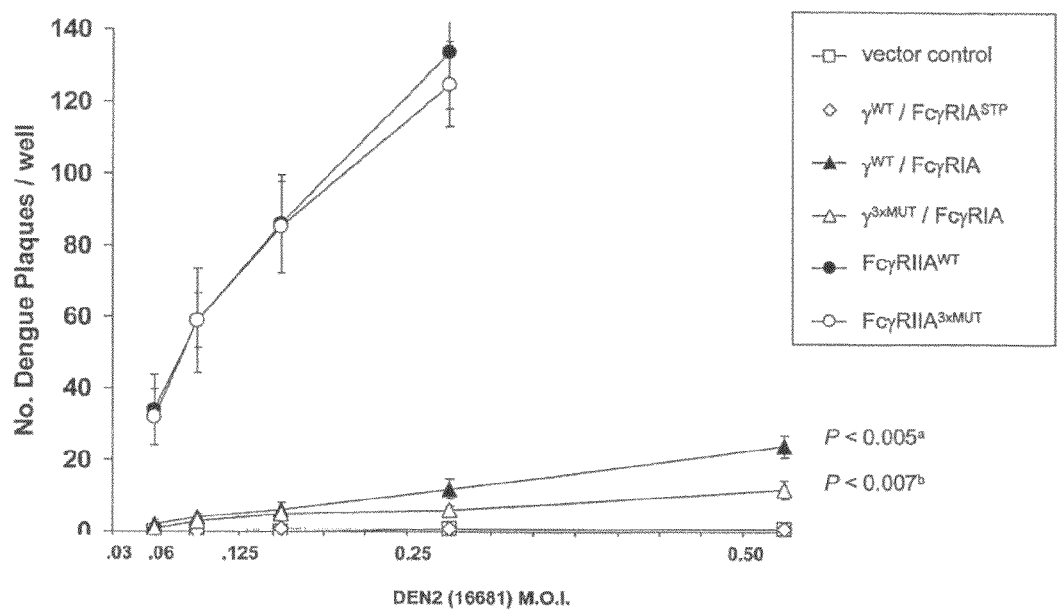

Dengue Immune Complex Infectivity is Greater in COS Cells Expressing FcγRIIA than FcγRIA Pooled human anti-dengue sera of broad dengue serotype neutralizing and hemagglutination-inhibiting capacity were used to prepare infectious dengue 2 immune complexes for presentation to the respective COS FcγR transfectants. This polyclonal serum pool, prepared from serologically screened American and Asian dengue fever patients, likely represents broad dengue virion antigenic specificity and IgG subclass diversity, so that any differences in results among COS transfectants should confidently reflect behavior specific to the respective FcγR. Two strains of dengue 2 virus were used to prepare immune complexes: i) a virulent strain, 16681, isolated from a patient with dengue hemorrhagic fever/shock syndrome during a South Asian epidemic that was marked by a high prevalence of complicated dengue fever (Halstead & Simasthien, "Observations Related to the Pathogenesis of Dengue Hemorrhagic Fever. II. Antigenic and Biologic Properties of Dengue Viruses and Their Association with Disease Response in the Host," *Yale J Biol Med* 42(5):276-92 (1970), which is hereby incorporated by reference in its entirety); and ii) the prototypic attenuated strain, New Guinea C (NGC) (Sabin, "Research on Dengue During World War II," *Am. Trop. Med. Hyg.* 1(1):30-50 (1952), which is hereby incorporated by reference in its entirety). The infectivity of preformed dengue 2 immune complexes in FcγRIA or FcγRIIA-expressing COS cells was measured by a conventional flavivirus plaque reduction neutralization assay method performed by infecting cells in suspension (Morens et al., "Simplified Plaque Reduction Neutralization Assay for Dengue Viruses by Semimicro Methods in BHK-21 Cells: Comparison of the BHK Suspension Test with Standard Plaque Reduction Neutralization," *J Clin Microbiol* 22(2):250-4 (1985), which is hereby incorporated by reference in its entirety). Cells were thus continuously exposed to virus immune complexes during the initial monolayer formation. Strain 16681 dengue 2 produced small (<1 mm), relatively homogeneous and sharply defined plaques in COS cells, whereas those formed by the NGC strain were larger (2 mm) and more irregular. The efficiency of dengue 2 plaque formation in the absence of antibodies was comparable among the FcγR and control (empty vector, $\gamma^{WT}$/FcγRIA$^{STP}$) transfectants, as shown in FIG. 10A. FIGS. 10B and 10C show the relative infectivity of strain 16681 (FIG. 10B) or NGC (FIG. 10C) dengue 2 immune complexes in signaling-competent ($\gamma^{WT}$/FcγRIA; FcγRIIA$^{WT}$) or signaling-incompetent ($\gamma^{3\times MUT}$/FcγRIA; FcγRIIA$^{3\times MUT}$) COS transfectants. COS cells transfected with the pcDNA5/FRT "empty" vector or with γ-chain only ($\gamma^{WT}$/FcγRIA$^{STP}$) served as controls. In ten such experiments performed in duplicate or triplicate, the infectivity of partially neutralized dengue immune complexes was enhanced in both γ/FcγRIA and FcγRIIA-expressing COS cells, but this effect was consistently and strikingly greater in FcγRIIA than in FcγRIA transfectants. Abrogation of FcγRIA signaling competency by mutation of all γ-chain cytoplasmic tail Tyr residues led to reduced dengue immune complex infectivity, but mutation of the analogous FcγRIIA cytoplasmic tyrosine residues had no apparent effect. No difference was observed between the two dengue virus strains with respect to the degree of enhanced immune complex infectivity among the FcγR transfectants. To further compare the relative importance of signal transduction capacity for FcγRIA and FcγRIIA-mediated enhancement, immune complexes formed with a range of antibody and dengue 2 virus concentrations were presented to COS cells expressing the respective native or mutant receptors. The results are illustrated in FIGS. 11A and 11B. Strain 16681 dengue 2 virus was used for these experiments because its distinctive plaque morphology allowed for more precise counting than did strain NGC. Enhanced immune complex infectivity was observed only in FcγR-expressing cells, independent of receptor signaling competency, compared to control transfectants. Dengue immune complex infectivity was significantly greater in FcγRIIA than in FcγRIA-expressing COS cells over the range of virus and antibody concentrations examined. Complete abrogation of signaling competency significantly diminished FcγRIA-enhanced infection, but remarkably had no discernable effect on immune complex infectivity enhanced by FcγRIIA engagement.

Example 12

Figure 12A:
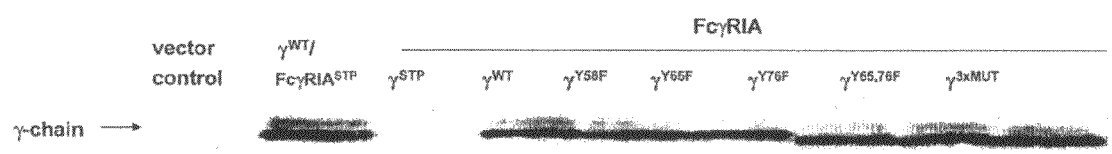
FIGS. 12A-D are a Western blot (FIG. 12A) and graphs (FIGS. 12B-D) showing that FcγRIA-mediated phagocytosis and dengue immune complex infectivity are proportionately reduced by selective γ-chain mutation. COS cells were transfected with bicistronic vectors comprised of γ-chain alone ($\gamma^{WT}$/FcγRIA$^{STP}$), FcγRIA alone ($\gamma^{STP}$/FcγRIA) or FcγRIA and γ-chain in which its cytoplasmic tail residues (Y58, Y65, Y76) were individually or multiply (Y65, 76; 3×MUT) mutated by Tyr-to-Phe residue substitution. Results are from an experiment performed in triplicate.
Figure 12B:
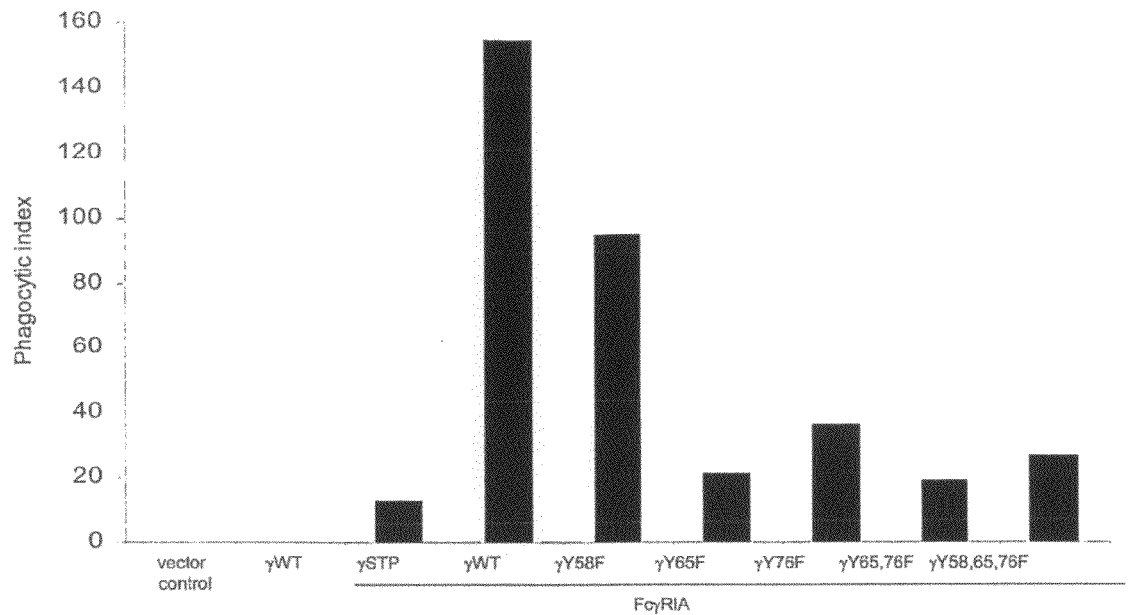
Figure 12C:
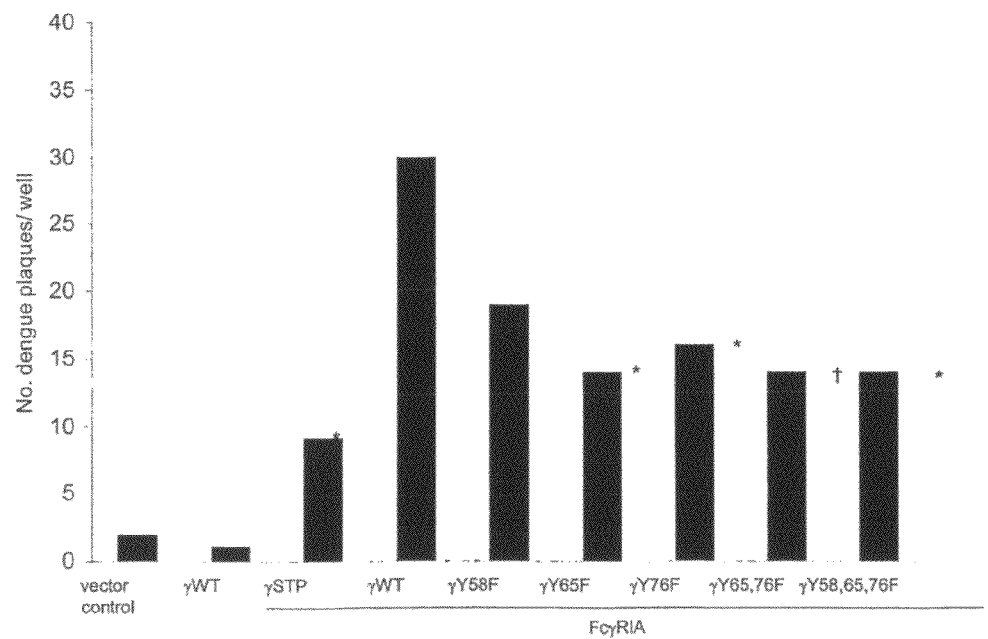

FcγRIA-Mediated Phagocytosis and Immune Complex Infectivity are Proportionately Reduced by Selective γ-Chain Mutation Previous molecular dissection of phagocytosis by COS cells that expressed FcγRIA-γ-chain chimeras revealed a hierarchy of effects of γ-chain Tyr-to-Phe residue changes on phagocytosis (Kim et al., "Fcγ Receptors Differ in Their Structural Requirements for Interaction with the Tyrosine Kinase Syk in the Initial Steps of Signaling for Phagocytosis," *Clin Immunol* 98(1):125-32 (2001), which is hereby incorporated by reference in its entirety). To test the hypothesis that FcγRIA-mediated phagocytosis and dengue immune complex infectivity involve a common mechanism, a panel of bicistronic vectors were prepared comprising FcγRIA and γ-chain versions with selected tyrosine residue mutations, and phagocytosis and dengue immune complex infectivity were measured in parallel among this COS transfectant panel. COS cells transfected with the empty vector, or those expressing only γ-chain ($\gamma^{WT}$/FcγRIA$^{STP}$) or FcγRIA ($\gamma^{STP}$/FcγRIA), served as controls. Equivalent FcγRIA expression among the FcγRIA transfectants was verified by flow cytometry; in accord, γ-chain abundance, measured by Western blot and densitometry, was comparable among the respective COS transfectants, as shown in FIG. 12A. Equivalent binding of opsonized yeast particles was observed among the COS cells that expressed FcγRIA. Quantitative phagocytosis of opsonized yeast particles by the COS transfectants is shown in FIG. 12B. COS transfectants that did not express FcγRIA exhibited no phagocytic activity. The highest phagocytic indices were observed in COS cells that expressed FcγRIA associated with γ-chain in native form. COS cells that expressed FcγRIA unassociated with γ-chain had the lowest receptor surface density and exhibited only trivial phagocytosis. Single or double γ-chain ITAM tyrosine mutations were accompanied by up to a 10-fold reduction in phagocytic activity. Mutation of the γ-chain non-ITAM tyrosine residue (Y58F) also led to a modest reduction in phagocytic activity. In parallel, the relative infectivity of dengue immune complexes was measured among the COS transfectants, as shown in FIG. 12C. Dengue immune complex infectivity was essentially neutralized in control COS cells that did not express FcγRIA. Immune complex infectivity was increased more than 10-fold in COS cells that expressed FcγRIA associated with γ-chain in native form. Infectivity was also significantly (P<0.05; two-tailed t-test) increased in COS cells that expressed FcγRIA without a γ-chain, but at a much lower level. Both single and double Tyr-to-Phe mutations of the γ-chain tail ITAM were accompanied by a parallel reduction in phagocytosis and immune complex infectivity that was, in each case, statistically significant (P<0.05 to 0.01; two-tail t-test) compared to results with FcγRIA associated with a γ-chain. Point mutation of upstream Tyr residue 58 was associated with reduced immune enhancing activity that was not significant (P>0.05) and that did not add to the effect of the ITAM mutations. These comparative findings were consistent over a range of virus and antibody concentrations.

Figure 12D:
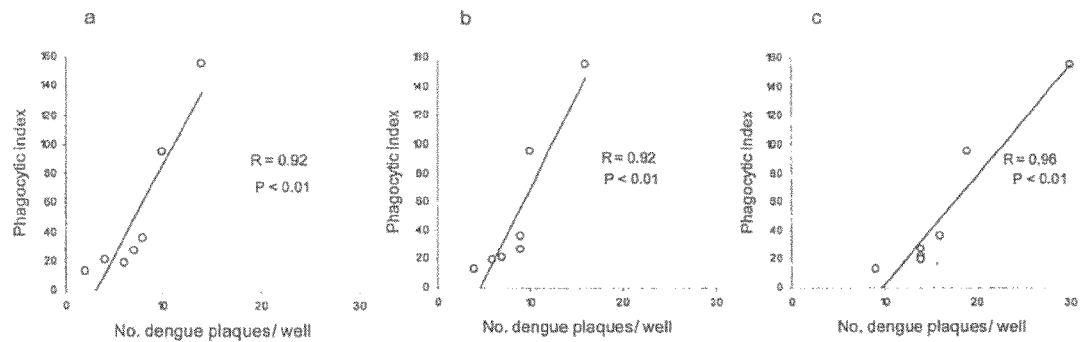

To discern if phagocytosis and immune complex internalization might share similar mechanisms, a linear regression analysis was performed and a highly significant correlation (P<0.01) was found between phagocytic and immune enhancement capacities among the COS transfectant panel incubated with dengue immune complexes formed with serial MOI of dengue virus (0.25, 0.5, 1.0) and dengue antiserum (1/1000), as shown in FIG. 12D. Collectively, these data point to a shared pathway for phagocytosis and enhanced dengue immune complex infectivity mediated by FcγRIA and its accessory γ-chain.

Discussion of Examples 1-12

FcγR-mediated phagocytosis, internalization of relatively large opsonized particles, and endocytosis, internalization of soluble immune complexes, are biologically distinguishable processes: for both, ligand-clustered receptors are internalized, but only for phagocytosis does FcγR signaling competency appear essential to complete the entry process. For example, cells expressing FcγRIA bereft of a γ-chain, or FcγRIIA with tail ITAM alterations, may internalize soluble IgG complexes, but not opsonized particles (Davis et al., "Two Distinct Regions of FcγRI Initiate Separate Signalling Pathways Involved in Endocytosis and Phagocytosis," Embo J 14(3):432-41 (1995); Lowry et al., "Functional Separation of Pseudopod Extension and Particle Internalization During Fcγ Receptor-mediated Phagocytosis," J Exp Med 187(2):161-76 (1998); Odin et al., "Regulation of Phagocytosis and [Ca$^{2+}$]$_i$ Flux by Distinct Regions of an Fc Receptor," Science 254(5039):1785-8 (1991); Van den Herik-Oudijk et al., "Identification of Signaling Motifs within Human FcγRIIa and FcγRIIb Isoforms," Blood 85(8):2202-11 (1995), which are hereby incorporated by reference in their entirety). Virus immune complexes are interesting ligands in this respect, since their size and infectivity depends on the nature and quantity of coating antibody (Almeida & Waterson, "The Morphology of Virus-antibody Interaction," Adv Virus Res 15:307-38 (1969); Parren & Burton, "The Antiviral Activity of Antibodies in Vitro and in Vivo," Adv Immunol 77:195-262 (2001), which are hereby incorporated by reference in their entirety), and they may have access to other routes of internalization that utilize virus receptors which themselves may trigger signaling events (Smith & Helenius, "How Viruses Enter Animal Cells," Science 304(5668):237-42 (2004), which is hereby incorporated by reference in its entirety).

As described in Examples 1-12, the influence of FcγRIA and FcγRIIA on the infectivity of dengue immune complexes prepared with human neutralizing dengue antibodies was compared. Signaling-competent and signaling-incompetent versions of these receptors were expressed in dengue-permissive COS cells to discern whether dengue immune complex internalization, like that of opsonized large particles, depended on the receptors' activation properties.

This approach, using COS transfectants to measure dengue immune complex infectivity after Fc receptor engagement, offered a number of advantages over studies that have employed macrophages or macrophage-like cell lines. First, FcγRIA and FcγRIIA were examined individually in isolation from other FcγR classes or unrelated macrophage receptors that may alter their function on such cells (Daëron, M., "Fc Receptor Biology," Annu Rev Immunol 15:203-34 (1997); Mukhopadhyay et al., "The Potential for Toll-like Receptors to Collaborate with Other Innate Immune Receptors," Immunol 112(4):521-30 (2004); Ortiz-Stern & Rosales, "Crosstalk Between Fc Receptors and Integrins," Immunol Lett 90(2-3):137-43 (2003), which are hereby incorporated by reference in their entirety). Second, FcγRIA and FcγRIIA concentrations on the surface of COS transfectants were comparable (~30,000 to 40,000 molecules per cell), which is generally not the case for monocyte/macrophages in which abundance of these receptors is differentially regulated by inflammatory mediators and affected by culture conditions (Jungi & Hafner, "Quantitative Assessment of Fc Receptor Expression and Function During in Vitro Differentiation of Human Monocytes to Macrophages," Immunol 58(1):131-7 (1986); van de Winkel & Anderson, "Biology of Human Immunoglobulin G Fc Receptors," J Leukoc Biol 49(5):511-24 (1991), which are hereby incorporated by reference in their entirety), e.g., the surface concentration of FcγRIIA on unstimulated THP-1 cells was ~10-fold higher than that of FcγRIA (see Table 1). The determinations of FcγRIA and of FcγRIIA COS cell surface concentrations were within the range reported for FcγR on human peripheral blood monocyte/macrophages (Jungi & Hafner, "Quantitative Assessment of Fc Receptor Expression and Function During in Vitro Differentiation of Human Monocytes to Macrophages," Immunol 58(1):131-7 (1986); van de Winkel & Anderson, "Biology of Human Immunoglobulin G Fc Receptors," J Leukoc Biol 49(5):511-24 (1991), which are hereby incorporated by reference in their entirety). Interestingly, it was found that FcγRIA surface concentrations were significantly higher when this receptor was associated with γ-chain than without it, in accord with the γ-chain requirement for efficient FcγRIA assembly and surface expression in vivo (Takai, T., "Roles of Fc Receptors in Autoimmunity," Nat Rev Immunol 2(8):580-92 (2002); Takai et al., "FcR γ Chain Deletion Results in Pleiotrophic Effector Cell Defects," Cell 76(3):519-29 (1994); van Vugt et al., "FcR γ-Chain is Essential for Both Surface Expression and Function of Human FcγRI (CD64) in Vivo," Blood 87(9):3593-9 (1996), which are hereby incorporated by reference in their entirety), and in contrast to the reduced FcγRIA expression in COS cells when separate vectors are used to deliver FcγRIA and γ-chain genes (Miller et al., "A Novel Role for the Fc Receptor γ Subunit: Enhancement of FcγR Ligand Affinity," J Exp Med 183(5):2227-33 (1996), which is hereby incorporated by reference in its entirety). Since FcγRIA and γ-chain are non-covalently linked at the transmembrane level (Harrison et al., "The Interaction Between Human FcγRI and the γ-Chain is Mediated Solely via the 21 Amino Acid Transmembrane Domain of FcγRI," *Mol Membr Biol* 12(4):309-12 (1995); Kim et al., "Fcγ Receptor Transmembrane Domains: Role in Cell Surface Expression, γ Chain Interaction, and Phagocytosis," *Blood* 101(11):4479-84 (2003); Miller et al., "A Novel Role for the Fc Receptor γ Subunit: Enhancement of FcγR Ligand Affinity," *J Exp Med* 183(5):2227-33 (1996), which are hereby incorporated by reference in their entirety), it is unlikely that mutations in the γ-chain cytoplasmic domain affected this association. That the FcγRIA surface concentration was the same when associated with a native or mutated γ-chain lends further support to this conclusion. Abrogation of Fc receptor signaling competency was verified by the significant reduction in phagocytic activity upon ITAM mutation. The low-level particle internalization observed among rosetted signaling-incompetent FcγR transfectants was not surprising, since many fibroblast cell types exhibit inherent phagocytic activity (Rabinovitch, M., "Professional and Nonprofessional Phagocytes: An Introduction," *Trends Cell Biol* 5(3):85-7 (1995), which is hereby incorporated by reference in its entirety).

The extracellular portion of FcγRIA was earlier reported to be sufficient for increased dengue immune complex infectivity in COS cells, although a concurrent γ-chain modulating effect was not ruled out (Schlesinger & Chapman, "Influence of the Human High-affinity IgG Receptor FcγRI (CD64) on Residual Infectivity of Neutralized Dengue Virus," *Virology* 260(1):84-8 (1999), which is hereby incorporated by reference in its entirety). As described in Examples 1-12, the question of a possible γ-chain role in dengue immune enhancement has been examined by using bicistronic vectors designed to assure uniform co-expression of FcγRIA and γ-chain versions among the cotransfectants, which was confirmed by flow cytometry and biochemically. It was found that enhanced immune complex infectivity mediated by FcγRIA was optimal when the receptor was associated with a γ-chain in its native form, and that abrogation of γ-chain ITAM signaling capacity by Tyr-to-Phe mutation, or expression of FcγRIA without a γ-chain, reduced but did not eliminate this function. The results with FcγRIA are interpreted to reflect at least two virus immune complex internalization mechanisms at work: the first, a γ-chain signaling-dependent event wherein infectious virus immune complex aggregates of sufficient size triggered a classical phagocytosis entry pathway. This mechanism is suggested by the striking correlation between phagocytic capacity and immune complex infectivity among COS cells that expressed FcγRIA associated with γ-chain ITAM mutants. Indeed, antibody-virus complexes, including opsonized flaviviruses, can form lattice structures of considerable size (Almeida & Waterson, "The Morphology of Virus-antibody Interaction," *Adv Virus Res* 15:307-38 (1969); Fauvel et al., "Immune Electron Microscopy of Arboviruses," *Am J Trop Med Hyg* 26(4):798-807 (1977), which are hereby incorporated by reference in their entirety), so that for dengue virus (50 nm diameter), immune complexes comprised of as few as 10 virions, i.e., a 500 nm "particle", might be predicted to trigger phagocytosis (Aderem & Underhill, "Mechanisms of Phagocytosis in Macrophages," *Annu Rev Immunol* 17:593-623 (1999), which is hereby incorporated by reference in its entirety). The second, a less efficient entry mechanism, relied simply on concentrating partially neutralized virions onto the cell for entry by a parallel endocytosis mechanism. Importantly, no effect of isolated γ-chain expression on virus or virus immune complex infectivity was observed, arguing against enhanced replication explained by γ-chain association with a cell protein other than FcγRIA.

FcγRIIA was strikingly more efficient than FcγRIA in enhancing dengue immune complex infectivity. Abolishing FcγRIIA ITAM signaling competency led to impaired phagocytosis, but unlike with signaling-incompetent FcγRIA, immune enhancement appeared to be unaffected. These experiments do not offer an immediate explanation for the divergent findings with these FcγR. FcγRIIA preferentially binds immune complexes and exhibits a fast off-rate (Maenaka et al., "The Human Low Affinity Fcγ Receptors IIa, IIb, and III Bind IgG with Fast Kinetics and Distinct Thermodynamic Properties," *J Biol Chem* 276(48):44898-904 (2001), which is hereby incorporated by reference in its entirety), whereas FcγRIA preferentially binds monomeric IgG, with notably high affinity. Ligand-clustered Fc receptors, including FcγRIIA, are known to concentrate in cell membrane regions, e.g., lipid rafts, rich in a variety of signaling molecules and potential virus receptor engagement sites (Katsumata et al., "Association of FcγRII with Low-density Detergent-resistant Membranes is Important for Cross-linking-dependent Initiation of the Tyrosine Phosphorylation Pathway and Superoxide Generation," *J Immunol* 167(10): 5814-23 (2001); Kwiatkowska & Sobota, "The Clustered Fcγ Receptor II is Recruited to Lyn-containing Membrane Domains and Undergoes Phosphorylation in a Cholesterol-dependent Manner," *Eur J Immunol* 31(4):989-98 (2001); Manes et al., "Pathogens: Raft Hijackers," *Nat Rev Immunol* 3(7):557-68 (2003); Simons & Toomre, "Lipid Rafts and Signal Transduction," *Nat Rev Mol Cell Biol* 1(1):31-9 (2000), 2(3):216 (2001) (erratum), which are hereby incorporated by reference in their entirety). It seems reasonable to speculate that FcγRIIA is better equipped than is FcγRIA to utilize alternative signaling pathways and entry mechanisms made available by relocation to such sites where weakly bound immune complexes might be more easily transferred to favorable entry pathways. Bispecific monoclonal antibodies that directed dengue virus to FcγRIIA or non-Fc receptor proteins on the surface of U937 human macrophage-like cells enhanced infection, arguably by such an alternate entry mechanism (Mady et al., "Antibody-dependent Enhancement of Dengue Virus Infection Mediated by Bispecific Antibodies Against Cell Surface Molecules Other Than Fcγ Receptors," *J Immunol* 147(9):3139-44 (1991), which is hereby incorporated by reference in its entirety).

These findings emphasize the conditional nature of virus neutralization or enhancement by antibody and suggest an approach to further investigate an aspect of dengue-antibody interaction that is tied to both the protective and pathologic immune response to infection by this virus.

Example 13

Generation of CV-1 and Vero Cell Lines that Constitutively Express Human Fcγ Receptors to Measure Dengue Neutralizing and Enhancing Antibodies in Human Sera As described in Examples 1-12, human Fcγ receptors of different classes transiently expressed in COS-7 monkey kidney cells mediate enhanced infectivity of dengue viruses by human dengue antisera. Human Fcγ receptor genes have also been constitutively engineered into CV-1 and Vero monkey kidney cells that are conventionally used to measure neutralizing antibodies against flaviviruses and other viruses, thereby creating a novel assay that also measures immune enhancing antibodies. To accomplish this, the Flp recombinase-mediated integration system ("Flp-In System", Invitrogen Corp.) was adopted. This system allows for stable integration and constitutive expression of Fc receptors, individually or in combination (if multiple FRT sites have been inserted), at a random, fixed chromosomal site(s).

Example 14

Preparation of Fcγ Receptor-Expressing Stable CV-1 Cell Lines

A CV-1 cell line that incorporates a single FRT site (CV-1/FRT) was purchased from Invitrogen Corp., and the stable Fc receptor-expressing cell lines were prepared by following the manufacturer's instructions. Briefly, CV-1/FRT cells bear zeocin antibiotic resistance and lacZ (lacZ-Zeo locus) genes so that they remain viable in zeocin (but not hygromycin) selection media, and produce β-galactosidase that results in blue cell staining upon addition of x-gal. The Fc receptor gene of interest in a pcDNA5/FRT vector that incorporates a hygromycin resistance gene was co-transfected with plasmid pOG44 that encodes a recombinase. Lipofectamine 2000 was used for all transfections. If properly integrated, the lacZ-Zeo locus is disrupted, zeocin resistance is lost, hygromycin resistance is acquired, and FcR-expressing cells survive in hygromycin-containing media and fail to stain blue after x-gal treatment. Each of the transfectants of the present invention has met these criteria. FcγRIA/γ-chain genetic sequences were confirmed by DNA sequence analysis following cloning of each construct into the pcDNA5/FRT vector. Plasmid expression constructs were propagated in $E.\ coli$ and purified using standard methods. γ-Chain expression in constitutively expressing CV-1 lines was demonstrated by immunoprecipitation and Western blot using anti-γ chain rabbit antiserum. Frequencies of FcγR-expressing cells and density of surface expression among constitutive transfectants were measured by flow cytometry using FcγRI (CD64) phycoerythrin-labeled monoclonal antibodies.

Stable CV-1 cell lines expressing signaling-competent and signaling-incompetent forms of FcγRIA and FcγRIIA-H131 have been prepared. The signaling-incompetent transfectants were prepared by PCR-mediated site-directed mutagenesis using the oligonucleotides designed to modify tyrosine residues ($Y_1$, $Y_2$, and $Y_3$) in the respective cytoplasmic signaling domains:

$Y_1$ETADGG$Y_2$MILNPRAPTDDDKNI$Y_3$LTL
(FcγRIIA cytoplasmic tail immunoreceptor tyrosine activation motif)

$Y_1$EKSDGV$Y_2$TGLSTRNQET$Y_3$ETL
(human FcγRIA γ-chain)

(Kim et al., "Fcγ Receptors Differ in Their Structural Requirements for Interaction with the Tyrosine Kinase Syk in the Initial Steps of Signaling for Phagocytosis," *Clin Immunol* 98(1):125-32 (2001), which is hereby incorporated by reference in its entirety). Specifically, tyrosine to phenylalanine (Y to F) substitutions were introduced in the amino acid sequence of FcγRI γ-chain sequence at positions 65 (Y65F) and 76 (Y76F), and in the amino acid sequence of FcγRIIA at positions 282 (Y282F) and 298 (Y298F). The cytoplasmic domains of these factors include conserved tyrosine-containing sequences (YXXL; bold above). A third tyrosine residue that is not in the YXXL context appears slightly upstream. These conserved sequences have been characterized as ITAMs (Ig gene family tyrosine activation motifs) and substitution of Y with F at these locations has been shown to disrupt ITAM function (Indik et al., "Molecular Dissection of Fcγ Receptor Mediated Phagocytosis," *Immunol Lett* 44:133-8 (1995), which is hereby incorporated by reference in its entirety).

Example 15

Preparation of Fcγ Receptor-Expressing Stable Vero Cell Lines

Vero cells used for flavivirus plaque assays were obtained from Dr. Karl Johnson (CDC, Atlanta). Single (Vero/FRT clone no. 42) or multiple (Vero/FRT clone no. 5) Flp recombination sites were stably introduced into Vero cells and the respective lines were cloned in zeocin selection medium following the manufacturer's instructions. Further cloning was performed by FACS. FRT site integration was verified by Southern blotting and the Vero/FRT lines have maintained stable growth in zeocin selection medium and remain β-galactosidase positive. The Fc receptor genes of interest were introduced exactly as with CV-1 cells (see Example 14). Table 2 summarizes the current status of stable CV-1 and Vero cell lines that express human Fc receptors. The CV-1 control, $\gamma^-$/CD64, $\gamma^{WT}$/CD64, and $\gamma^{3\times MUT}$/CD64 cell lines have been fully cloned, verified, and are being stored. The long-term stability of the rest of the clones remains to be confirmed by culture.

TABLE 2

Stable CV-1 and Vero Cell Lines Expressing Human Fc Receptors

| Fcγ Receptor | CV-1 | Vero |
|---|---|---|
| empty vector control | ✓ | ✓ |
| $\gamma^-$/CD64 | ✓ | ✓ |
| $\gamma^{WT}$/CD64 | ✓ | ✓ |
| $\gamma^{3\times MUT}$/CD64 | ✓ | n.d. |
| CD32$^{WT}$ (H131) | ✓ | ✓ |
| CD32$^{3\times MUT}$ (H131) | ✓ | n.d. |
| CD32$^{WT}$ (R131) | ✓ | ✓ |
| $\gamma^{WT}$/CD64 + CD32$^{WT}$-H131 (double integrant) | n/a | ✓ |

Vero cell lines that incorporated either single or multiple FRT recombination/integration sites were engineered. Signaling-competent (γWT) or signaling-incompetent (γ3XMUT; γ$^-$) versions of γ-chain/FcγRIA (CD64) or H131 and R131 allotypes of FcγRIIA (CD32) were engineered into CV-1/FRT or Vero/FRT cells. A Vero/FRT line (no. 5) with multiple integration sites was used to prepare a double integrant that expresses both CD64 and CD32 in native form.

Example 16

Indicator Anti-Dengue NS1 and E Monoclonal Antibodies

Figure 13:
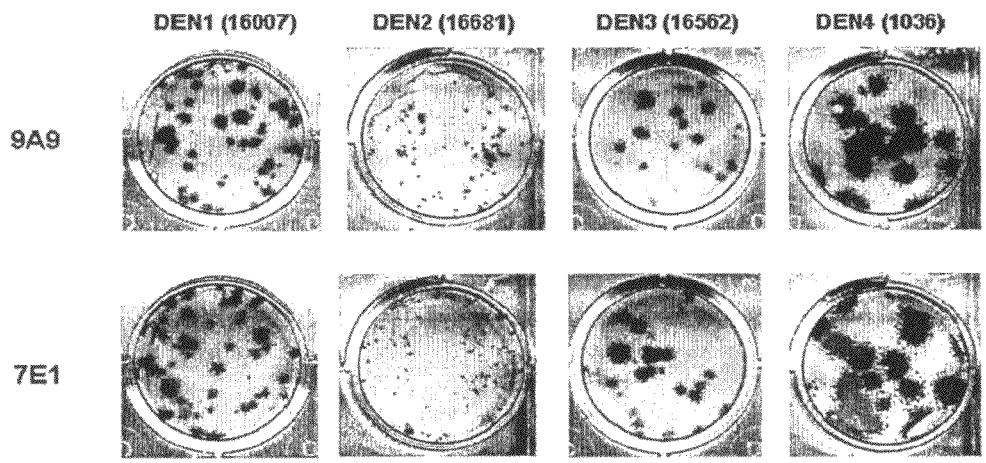
FIG. 13 is a series of images of dengue virus plaques in Vero cells visualized by indirect immunostaining with monoclonal antibodies against dengue nonstructural protein NS1 (9A9) or envelope protein E (7E1).
Figure 14:
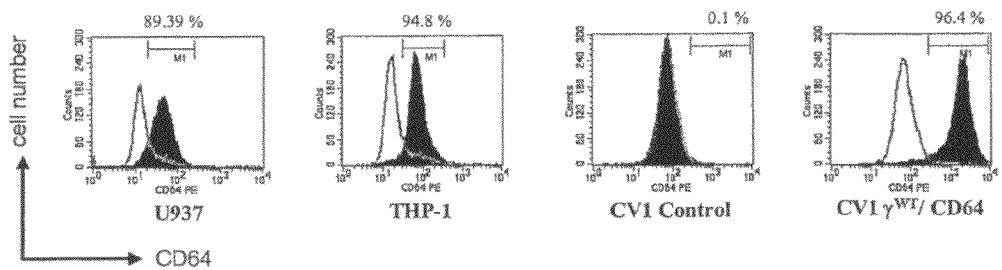
FIG. 14 is a series of flow cytometry histograms of γ-chain/FCγRIA (CD64) expression levels in CV-1 cell lines. RPE-labeled CD64 (mAb 10.1) monoclonal antibody (black) and mouse IgG1 isotype control (gray) were used to stain CV-1 transfectants. Human CD64-expressing U937 and THP-1 macrophage-like cells were used as controls. Results are representative of three determinations.

An anti-NS1 (Mab 9A9) and anti-E (Mab 7E1) antibody pair that exhibits properties especially useful for detecting dengue infection by plaque assay immunostaining (see FIG. 13) have been prepared and, after conjugation with fluorescent molecules, characterized by flow cytometric assay. Both are IgG1 antibodies that react equally well with each of the four dengue virus serotypes, and so provide generic dengue detection reagents.

Example 17

CD64 Expression Verified by Flow Cytometry

The CV-1/CD64 cell line was cloned by growth in selection medium and by FACS. CD64 expression and monoclonality of the cell line were verified by flow cytometry (see Table 3 and FIG. 14) using CD64 expressing U937 and THP-1 human macrophage-like cell lines as controls. Further, it was found that the CV-1/CD64 cell line expressed at least 10-fold more cell surface CD64 molecules than did U937 or THP-1 cells.

TABLE 3

Expression of Human γ-Chain/FcγRIA Complex (CD64) Measured by Flow Cytometry

| Cell Type | % positive cells (mean ± s.d.) | No. molecules/cells (mean ± s.d.) | (n) |
|---|---|---|---|
| U937 (10.6) | 89 ± 7.2 | 2990 ± 1866 | 3 |
| THP-1 | 93 ± 3.5 | 3264 ± 1292 | 6 |
| CV1 control | 0 | 0 | 3 |
| CV1 γ$^{WT}$/CD64 | 99 ± 0.2 | 40484 ± 3123 | 3 |

Example 18

γ-Chain Expression Verified by Immunoblot

Figure 15:
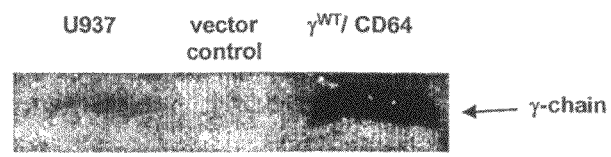
FIG. 15 is a Western blot confirming γ-chain expression. Cell lysates prepared from CV-1 cell lines ($5 \times 10^5$ cells/lane) and U937 ($1 \times 10^6$ cells/lane) were separated on a 15% SDS-PAGE gel, and immunoblotted using a monospecific rabbit antiserum against human γ-chain. U937 and CV-1 empty vector (integrated) cells served as positive and negative controls, respectively.

The bicistronic vector used to prepare the CV-1/CD64 transfectant ensured that cells that expressed CD64 would also express γ-chain. This was verified by Western blotting using rabbit IgG specific for human γ-chain, as shown in FIG. 15. U937 cell lysate provided γ-chain control. The intensity of staining was markedly greater with CV-1-derived γ-chain than that from U937 cells in accord with the greater CD64 abundance in the CV-1 transfectant.

Example 19

Function of the γ-Chain/CD64 Complex Verified by CV-1 Transfectant Phagocytosis

Figure 16:
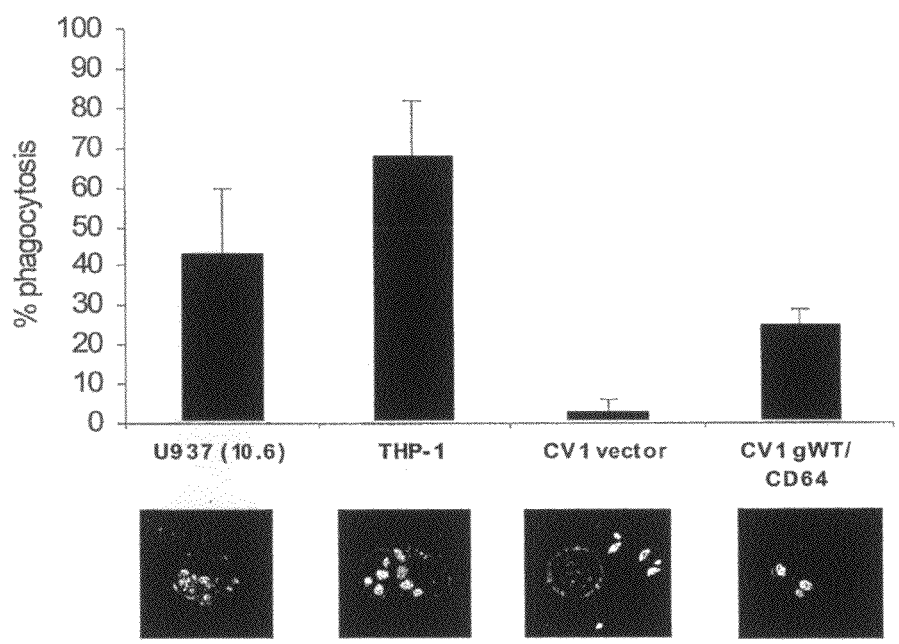
FIG. 16 is a graph and images relating to phagocytosis of opsonized C. albicans by CV-1 transfectants and human macrophage-like (THP-1) cells. Rabbit IgG-sensitized FITC stained yeast particles were incubated at 37° C. with the indicated cell types expressing $\gamma^{WT}$/FcγRIA (CD64) followed by counterstaining with ethidium bromide. Internalized particles stain differently from surface bound particles. Data represent mean and standard deviation of three independent experiments.

If properly constructed and expressed, the γ-chain/CD64 complex should confer phagocytic capability on the CV-1 transfectant. This was demonstrated to be the case by measuring internalization of opsonized yeast particles by the CV-1/CD64 transfectant, as shown in FIG. 16. CV-1 cells transfected by the "empty" vector served as a negative control. U937 and THP-1 macrophages served as a positive control.

Example 20

γ-Chain/CD64 Complex Constitutively Expressed in a CV-1 Cell Line Mediates Antibody-Dependent Enhancement of Dengue Virus A human dengue antiserum pool neutralized dengue virus at low dilution and enhanced dengue virus replication at high dilution in the stable CV-1/CD64 cell line as determined by direct plaque assay (see FIG. 17A). No such neutralization or enhancement was observed with normal pooled human sera, as shown in FIG. 17B. The results establish a conventional plaque assay to simultaneously measure dengue virus neutralization and enhancement. Because a stable cell line has been used in this Example, the cell line holds promise for use in kits to assay particular virus/antibody combinations for immune enhancement and neutralization.

Example 21

Comparative Immune Enhancement of Dengue Virus in Stable CV-1 Cell Lines that Constitutively Express Human FcγRIA (CD64) or FcγRIIA-H131 (CD32)

Examples 1-12 demonstrate that the H131 allotype of FcγRIIA was strikingly more effective than FcγRIA in mediating immune enhancement of dengue virus. FIG. 18 shows that this difference is also clearly demonstrable using CV-1 cells engineered to stably express γ-chain deficient FcγRIA or FcγRIIA-H131.

Example 22

Dengue Replication is Enhanced in Vero Cells that Express Human Fc Receptors

Figure 19:
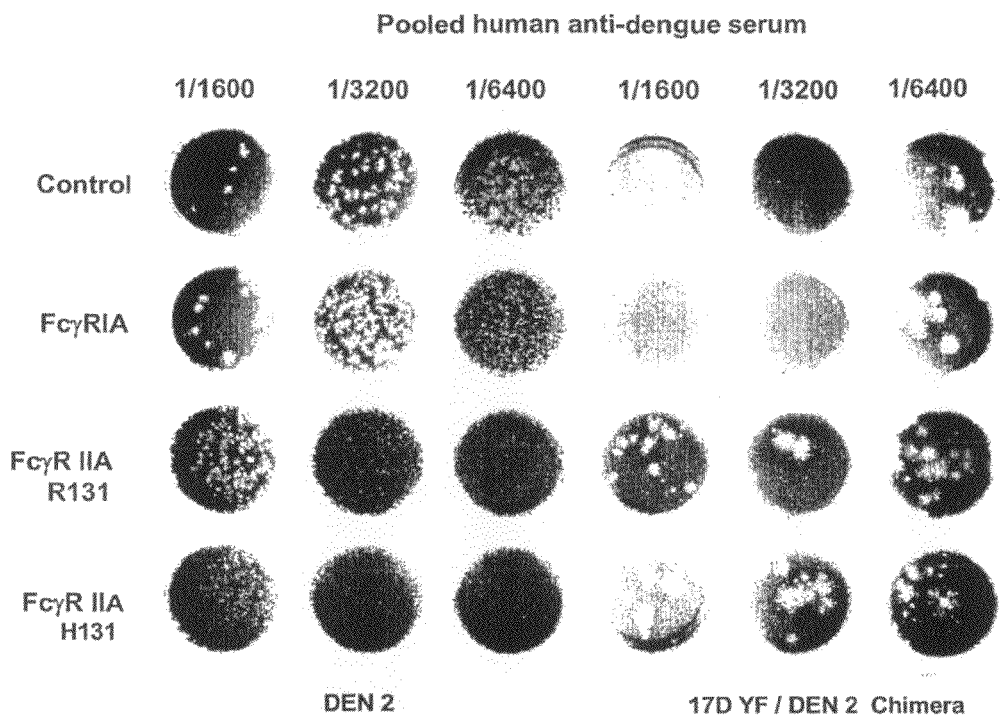
FIG. 19 is an image showing plaque formation by human antibody-complexed dengue 2 virus in Vero cell FcγR transfectants. Pre-formed virus-antibody complexes were prepared using New Guinea C dengue 2 virus or a candidate dengue 2 vaccine, yellow fever 17D/dengue 2 chimera (17D YF/DEN2) (Chambers et al., "Yellow Fever Virus/Dengue-2 Virus and Yellow Fever Virus/Dengue-4 Virus Chimeras: Biological Characterization, Immunogenicity, and Protection Against Dengue Encephalitis in the Mouse Model," *J Virol* 77(6):3655-68 (2003), which is hereby incorporated by reference in its entirety) and serial dilutions of pooled human dengue virus antisera before addition to a 24-well cluster plate containing Vero cells transiently transfected with human FcγR1A or FcγR11A allotypes H131 or R131. Mock-transfected Vero cells served as a control. The results are representative of three individual experiments.
Figure 20:
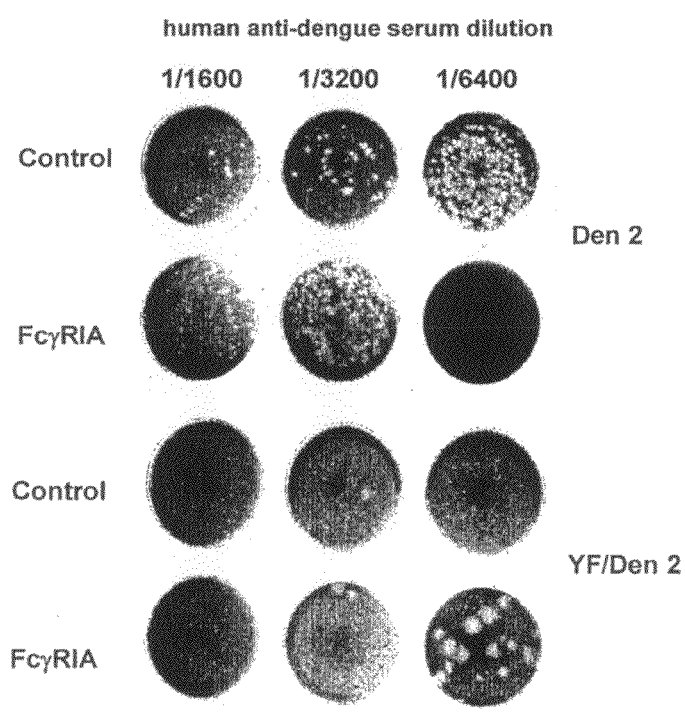
FIG. 20 is an image showing plaque formation by DEN2 virus and YF-DEN2 virus in a constitutive Vero cell FcγRIA transfectant.

The present method for simultaneously measuring neutralization and enhancement of dengue virus in human Fc receptor transfectants has been extended by transiently expressing CD64 and both allotypes (R131 and H131) of CD32 in Vero cells. This cell line is widely used to detect a wide range of medically important flaviviruses, including yellow fever, West Nile, and Japanese encephalitis viruses, and to measure neutralizing antibodies against them. Vero cells are also widely used to grow a number of disparate RNA (e.g., influenza, polio) and DNA viruses (e.g., herpes, pox) and to measure neutralizing antibodies against them. FIG. 19 shows that the infectivity of immune complexes formed using pooled human dengue antisera and dengue 2 virus (DEN 2) or a candidate dengue vaccine, yellow fever 17D vaccine/dengue 2 chimera (17D YF/DEN2), is enhanced in Fc receptor-expressing Vero cells. In accord with the work described in Examples 1-12, enhancement levels were considerably higher with CD32 than CD64 transfectants. The results offer strong support for use of this cell type for neutralization/enhancement assay design. Corresponding Fc receptor-expressing stable lines have been prepared (see Table 2). A constitutive FcγRIA transfectant, prepared from a Vero/FRT integrant that exhibits DEN2, YF, and YF/DEN2 (Chambers et al., "Yellow Fever Virus/Dengue-2 Virus and Yellow Fever Virus/Dengue-4 Virus Chimeras: Biological Characterization, Immunogenicity, and Protection Against Dengue Encephalitis in the Mouse Model," *J Virol* 77:3655-68 (2003), which is hereby incorporated by reference in its entirety) plaque characteristics identical to those of the parent Vero cell line, formed typical rosettes with opsonized SRBC and subserved neutralization escape with both DEN2 and YF-DEN2 virus, as show in FIG. 20.

Example 23

Simplified Assay to Simultaneously Measure Neutralizing and Immune-Enhancing Antibodies in Sera From Naturally-Infected or Vaccinated Subjects The stable FcγR transfectants used to dissect the molecular details of dengue virus neutralization escape (Examples 13-15; Table 2) offer a platform for development of a simplified Fc receptor-based assay that simultaneously measures neutralization and DEN immune-enhancing antibodies. These features were not previously available using conventional macrophage systems. This assay will first be applied to field samples to ensure that the laboratory engineered cells can be used to address whether candidate or actual vaccines are likely to cause immune enhancement against one or more viruses or virus strains. To accomplish this, a neutralization assay will be conducted using control cells and each of three constitutive transfectants representing native Class I or Class II FcγR to include: FcγRIA/γ-chain, FcγRIIA (H131), and FcγRIIA (R131). Although preliminary findings using pooled human dengue sera suggested no difference between H131 and R131 FcγRIIA allotypes with respect to neutralization escape, use of both with individual sera might disclose differences with respect to IgG2 incorporation in the dengue immune complexes since H131, but not R131, binds this IgG subclass. Prototypic strains of DEN1-4 and antibodies already in hand will be used to design the assay. If successful, incorporation of the assay as a tool for screening vaccines will be explored in the context of dengue vaccine trials conducted under the Pediatric Dengue Vaccine Initiative (PDVI). By utilizing the assay as a component of the vaccine development associated with the PDVI initiative, it is expected that the breadth of the assay will be demonstrated for specific dengue viruses and dengue antibodies.

Example 24

BHK21 Cell Line

CV-1 cells have been used for molecular dissection of FcγR-dengue immune complex interaction for several reasons: i) DEN2, DEN4, YF, and YF/DEN2 form quantifiable plaques in these cells; ii) collective knowledge of FcγR structure-function correlations, including immune complex internalization and phagocytosis of opsonized particles, largely derives from (transient) transfection systems that employed cells of CV-1 origin; iii) preliminary findings with FcγRIA constitutively displayed on CV-1 cells indicate that this receptor possesses relevant properties of native FcγRIA; and, iv) the CV-1 cells used herein bear a single FRT recombination site, so that it is reasonable to expect relative parity of expression among the panel of constitutive FcγR transfectants. This line, however, is infrequently used for DEN plaque assays. Vero cells and baby hamster kidney (BHK21) cells are regularly used for this purpose, with the former in routine use for yellow fever and chimeric YF/DEN plaque assays. To determine which FcγR-transfected cell line will be best suited for the combined neutralization/immune enhancement assay with respect to sensitivity of discrimination, specificity, and reproducibility, constitutive FcγRIA transfectants of CV-1, Vero, or BHK21 cell origin will be compared for these qualities. A stable high-expression CV-1/FcγRIA line and a Vero/FcγRIA line that awaits cloning and further characterization have been prepared (see Examples 14 and 15). An analogous constitutive BHK21/FcγR1A transfectant will be prepared using a commercially available BHK/FRT integrant (Invitrogen Corp.). The method is essentially identical to that used to prepare the CV-1 and Vero transfectants, although, here, an EF-1α promoter will substitute for the CMV promoter, which is down-regulated in BHK21 cells. The three cloned lines will then be assessed for stability and density of FcγRIA expression by FACS analysis and for neutralization or neutralization escape using mosquito cell-passaged prototypic strains of DEN1-4 and American and Asian wild strain DEN2 with monoclonal antibodies or sera directed at these viruses. To accommodate testing of relatively large numbers of sera (each likely available only in small volume), the semi-micro plaque reduction neutralization assay method of Morens and co-workers that employed BHK21 cells in suspension (Morens et al., "Simplified Plaque Reduction Neutralization Assay for Dengue Viruses by Semimicro Methods in BHK-21 Cells: Comparison of the BHK Suspension Test with Standard Plaque Reduction Neutralization," *J Clin Microbiol* 22(2):250-4 (1985), which is hereby incorporated by reference in its entirety) will be adopted. Since assays with CV-1 or Vero cells infected in suspension have been routinely performed, the method is immediately modifiable to conform with that used for the BHK21 assay. The same concern about serum supply prompts also measuring DEN immune complex infectivity in parallel by simple fluorescent focus assay (Chambers et al., "Yellow Fever Virus/Dengue-2 Virus and Yellow Fever Virus/Dengue-4 Virus Chimeras: Biological Characterization, Immunogenicity, and Protection Against Dengue Encephalitis in the Mouse Model," *J Virol* 77:3655-68 (2003); Schlesinger et al., "Cell Surface Expression of Yellow Fever Virus Non-structural Glycoprotein NS1: Consequences of Interaction with Antibody," *J Gen Virol* 71(Pt 3):593-9 (1990), which are hereby incorporated by reference in their entirety). Here, aliquots of immune complex-exposed cells will be delivered to multi-chamber slides for subsequent IF detection and counting of virus-infected cell foci.

Example 25

Screening of Clinical Sera for Immune Enhancing Antibodies

Sera from two different cohort studies that bear on the clinical expression of immune enhancement will be used. The first, secured from the United States Navy, is from a DEN2 outbreak of unexpectedly mild disease in a Peruvian population "primed" by DEN1 infection (Kochel et al., "Effect of Dengue-1 Antibodies on American Dengue-2 Viral Infection and Dengue Haemorrhagic Fever," *Lancet* 360:310-2 (2002); Watts et al., "Failure of Secondary Infection with American Genotype Dengue 2 to Cause Dengue Haemorrhagic Fever," *Lancet* 354:1431-4 (1999), which are hereby incorporated by reference in their entirety). The second sera are from yellow fever-immune subjects with heightened YF/DEN2 viremia after immunization with this monovalent chimera DEN vaccine candidate.

The incidence of severe forms of dengue fever in the course of epidemic dengue has been linked to the sequence in which different serotypes are introduced into a region. Experience with Asian and more recent Caribbean dengue epidemics pointed to second infection with DEN2 as especially likely to be accompanied by cases of complicated dengue fever. It was surprising, then, that epidemic DEN2 introduced into Iquitos, Peru, a region with established DEN1 circulation, was accompanied by only mild infection (Watts et al., "Failure of Secondary Infection with American Genotype Dengue 2 to Cause Dengue Haemorrhagic Fever," *Lancet* 354:1431-4 (1999), which is hereby incorporated by reference in its entirety). Subsequent investigation revealed that the new DEN2 was an American genotype and that monotypic DEN1 sera from the initial outbreak exhibited substantial unidirectional cross-serotype neutralizing activity against American DEN2. Little or no neutralizing activity, however, was observed against DEN2 of Asian genotypes associated with dengue hemorrhagic fever, such as NGC-related DEN2 present in Cuba since 1981 (Kochel et al., "Effect of Dengue-1 Antibodies on American Dengue-2 Viral Infection and Dengue Haemorrhagic Fever," *Lancet* 360:310-2 (2002), which is hereby incorporated by reference in its entirety). Sera from these studies will be used to repeat the neutralization assays in the FcγR transfectants and control cells of the present invention. The results will indicate if the Peruvian monotypic DEN1 antisera neutralizes American DEN2 in control and FcγR-bearing cells with equal efficiency, and if Asian DEN2 strain (weakly neutralized by these antibodies) is disproportionately more likely to escape neutralization (with or without enhancement) in the FcγR transfectants.

In the Peruvian DEN2 outbreak, it appeared that the relative avirulence of American DEN2 reflected "clinical attenuation" by DEN1 antibodies, perhaps by reducing viremia levels. Such balance, however, may be quite delicate if, as postulated, neutralization escape mutants were to emerge in the course of a similar DEN2 epidemic in a DEN1-immune population (Guzman et al., "Do Escape Mutants Explain Rapid Increases in Dengue Case-fatality Rates within Epidemics?," *Lancet* 355:1902-3 (2000), which is hereby incorporated by reference in its entirety). This intriguing possibility, experimentally testable with the assay of the present invention, might explain the rapid and progressive increase in severity of illness observed in the course of recent DEN2 epidemics in Cuba (Guzman et al., "Dengue Hemorrhagic Fever in Cuba, 1981: A Retrospective Seroepidemiologic Study," *Am J Trop Med Hyg* 42:179-84 (1990); Kouri et al., "Reemergence of Dengue in Cuba: A 1997 Epidemic in Santiago de Cuba," *Emerg Infect Dis* 4:89-92 (1998), which are hereby incorporated by reference in their entirety).

Example 26

Assay Performed with Yellow Fever and Yellow Fever/Dengue 2 Sera

Figure 23:
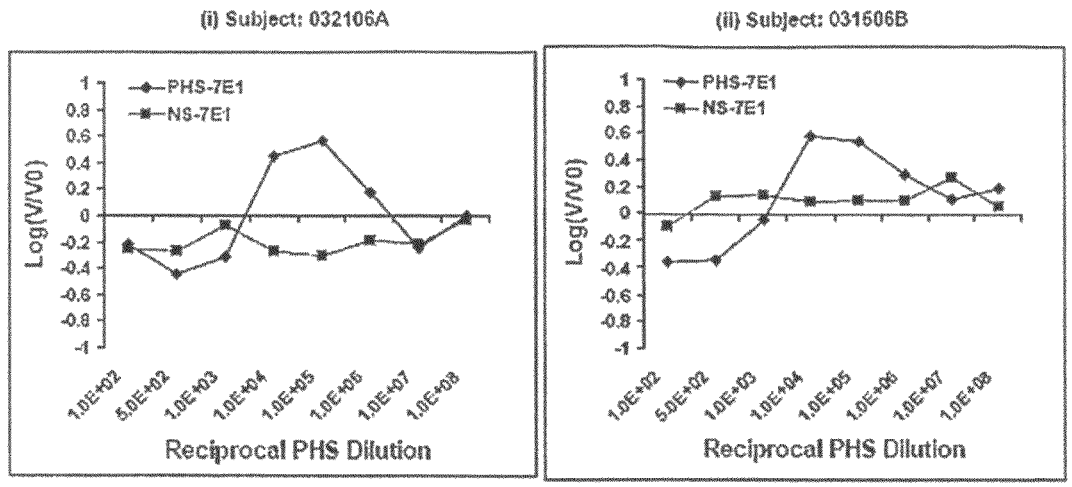
FIG. 23 is a set of graphs of Dengue virus 2 infectivity in the presence of normal serum (NS) and pooled dengue-immune human sera (PHS), showing that antibody-dependent enhancement is mediated by PHS, not normal human serum. Freshly isolated human peripheral blood mononuclear cells from two individuals (i and ii) were infected by Dengue virus 2 strain 16681 at MOI of 10 in the absence or presence of either PHS or normal serum (NS) at varying dilutions for two days, harvested and stained by labeled monoclonal antibody to Dengue virus 2 envelope E protein or an isotype-matched IgG control, as well as antibodies to T cells (CD3) or monocytes/macrophages (CD14), and then analyzed using flow cytometry. Antibody-dependent enhancement was only achieved with the dengue-immune human sera.

Heightened levels of viremia with an attenuated dengue vaccine candidate have been attributed to immune enhancement by cross-reacting yellow fever (YF) antibodies (Bancroft et al., "Dengue Virus Type 2 Vaccine: Reactogenicity and Immunogenicity in Soldiers," *J Infect Dis* 149:1005-10 (1984); Eckels et al., "The Association of Enhancing Antibodies with Seroconversion in Humans Receiving a Dengue-2 Live-virus Vaccine," *J Immun* 135(6):4201-4203 (1985); Scott et al., "Dengue 2 Vaccine: Dose Response in Volunteers in Relation to Yellow Fever Immune Status," *J Infect Dis* 148:1055-60 (1983), which are hereby incorporated by reference in their entirety). A similar observation has been recently reported among YF-immune subjects vaccinated with Acambis chimeric YF/DEN2. Collectively, these findings introduce concern about the capacity of YF vaccination to confer risk for complicated dengue fever (Guzman & Kron, "Threat of Dengue Haemorrhagic Fever after Yellow Fever Vaccination," *Lancet* 349:1841 (1997), which is hereby incorporated by reference in its entirety). The assays of the present invention will be used to measure possible immune-enhancing antibodies in sera from YF-immune subjects with heightened YF/DEN2 viremias. The assay will be performed using the YF/DEN2 vaccine and prototypic DEN1-4 strains. Multiple sera, in ample supply, from approximately 100 flavivirus-naïve subjects who participated in a series of 17D yellow fever vaccine evaluations conducted by Dr. Jacob Schlesinger (University of Rochester, Rochester, N.Y.) will be used to prepare a pool of potentially immune-enhancing antibodies for screening with the FcγR transfectant assay of the present invention. Pooled flavivirus antibody-free human sera will be used as a control. The assay will be performed in a checkerboard fashion using relatively low serum dilutions and virus concentrations since little or no neutralization of the chimera (or any dengue virus) by monotypic yellow fever antibodies stimulated by vaccination is anticipated. DEN2-neutralizing IgG Mabs of substantial titer from mice hyperimmunized with YF17D vaccine have, however, been isolated (Schlesinger et al., "Monoclonal Antibodies Distinguish Between Wild and Vaccine Strains of Yellow Fever Virus by Neutralization, Hemagglutination Inhibition, and Immune Precipitation of the Virus Envelope Protein," *Virol* 125:8-17 (1983), which is hereby incorporated by reference in its entirety). An increased efficiency of plaque formation in the FcγR transfectants will be regarded as immune enhancement, subject to statistical analysis as described in above.

Example 27

Detect Infectivity by Flow Cytometric Analysis

Flow cytometry has been used to detect antibody-dependent enhancement and neutralization of dengue virus in human peripheral blood mononuclear cells (PBMCs). Since previous studies have indicated that monocytes could be major target cells for dengue infection in the presence of enhancing antibodies (Kliks, "Antibody-enhanced Infection of Monocytes as the Pathogenetic Mechanism for Severe Dengue Illness," *AIDS Res Human Retroviruses* 6:993-8 (1990), which is hereby incorporated by reference in its entirety), and having established that the 7E1 and 9A9 anti-dengue E and NS1 protein antibodies can detect dengue antigen specifically in cell lines, these reagents were applied to DV infection using primary human peripheral blood mononuclear cells (PBMCs).

Generally, freshly isolated PBMCs were exposed to a virulent strain of Dengue virus 2 (16681) in the presence or absence of pooled dengue-immune human sera (PHS), and infection was assessed using novel fluorescent dye-labeled monoclonal antibodies (MAb) against Dengue virus nonstructural protein NS1 (MAb 9A9) or envelope E protein (MAb 7E1) by multi-color flow cytometric analysis.

In a representative experiment shown in FIG. 21, freshly isolated PBMCs were infected in the presence or absence of pooled dengue-immune human sera (PHS) at different dilutions including 1/100, 1/500, 1/1000, and then 10-fold serial dilution up to $1/10^8$. Infected cells were harvested 2 days later, and infectivity was analyzed by flow cytometry: DV-infected cells were harvested by gentle scraping, then washed twice with PBS, fixed and permeabilized with 500 μl of lysing buffer (BD), votexed gently, and incubated at room temperature for 10 minutes. The cells were then washed once with PBS and re-suspended in 500 μl of PBS, and 500 μl of Perm 2 (BD biosciences) were added to each tube, mixed, and the cells incubated for 10 minutes at room temperature. After permeabilizing, the cells were washed with PBS and re-suspended with 10% human AB serum in PBS, then stained for 30 minutes at room temperature with Alexa488-labeled 7E1 and murine anti-human antibodies specific for monocytes (FITC-CD14), B cells (PE-CD19), and T cells (PE-Cy5-CD3). Labeled murine IgG1 antibodies were used as a staining control. After staining, cells were washed twice with PBS and re-suspended in 1% formaldehyde before being analyzed using either a FACSCalibur or a LSRII flow cytometer (BD Immunocytometry Systems) in combination with either the CellQuest (BD Biosciences) or FlowJo (TriStar) software. The results are shown in FIG. 21. The percentage of monocytes that were also positive for the E antigen is also indicated. No cells were positive without the addition of virus; more than 3% of the cells were positive when virus was added. High concentrations of antibodies resulted in neutralization, and very low concentrations of the same antibody preparation led to enhancement. The maximal level of ADE was achieved at $1/10^5$ dilution of PHS.

Having shown that DV infection can be detected relatively quickly, in two days instead of five days by traditional plaques assay, whether ADE could be detected by this method was next examined. Experiments were performed as described for FIG. 21, except that normal serum (NS) from a dengue naïve individual was used in parallel to PHS. As shown in FIG. 22, the results from two subjects [(i) & (ii)] showed that although the NS had either modest "neutralizing" (subject (i)) or "enhancing" (subject (ii)) activity, these activities hardly changed with progressive dilution of the NS, indicating the NS does not contain dengue specific antibody. In contrast, as shown in FIG. 23, PHS showed neutralizing activity at 1/100 to 1/1000 dilution, and enhancing activity that peaked at 1/10,000 to 1/100,000 dilutions of the same PHS. This approach (using flow cytometry to measure infectivity) may also be applied to the assays of the present invention, substituting recombinant Fc receptor-expressing cells for the native PBMCs.

Figure 24:
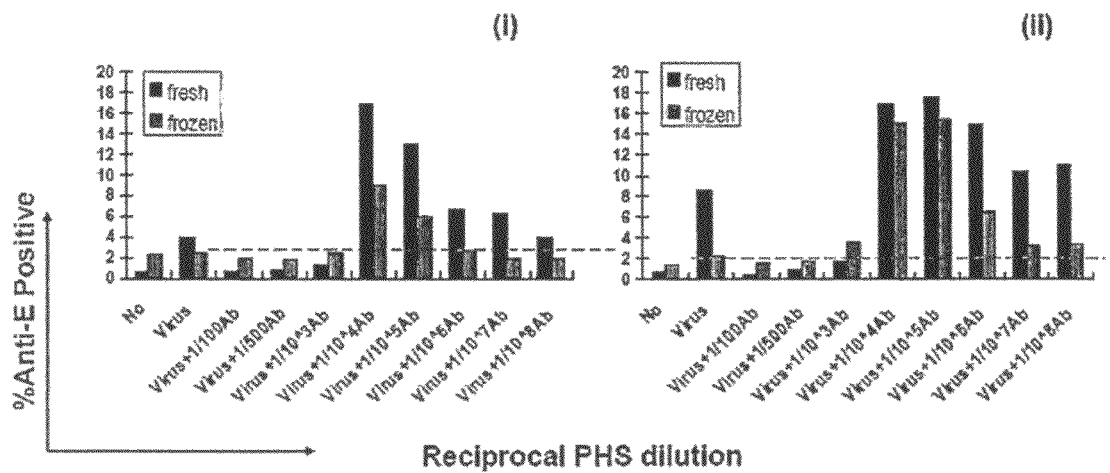
FIG. 24 is a set of graphs of Dengue virus infectivity and antibody-dependent enhancement capacity in fresh versus frozen cells. Freshly isolated (closed bars) or frozen and resurrected (hatched bars) human peripheral blood mononuclear cells from two individuals (i and ii) were infected by Dengue virus 2 strain 16681 at MOI of 10 in the absence or presence of pooled human serum (PHS) at varying dilution for two days, then harvested and stained by labeled monoclonal antibody to Dengue virus 2 envelope E protein or an isotype-matched IgG control, as well as antibodies to T cells (CD3) or monocytes/macrophages (CD14), then analyzed using flow cytometry. These results show that fresh monocytes/macrophages are more easily infected than frozen cells in the absence of PHS; frozen cells, nonetheless, could also mediate antibody-dependent enhancement in the presence of highly diluted PHS.

Since it would be desirable to perform the above neutralization and ADE assay using cryo-preserved cells, so that clinical cohort samples could be used, and experiments can be better organized to reduce systematic error, infection and ADE in freshly-isolated versus frozen cells was next compared. In two subjects, parallel experiments were performed using either fresh or frozen cells obtained from the same blood drawn. PBMCs were infected in the presence or absence of PHS at a range of dilutions. Infected cells were harvested 2 days later, and stained with Alexa488 labeled 7E1 in conjunction with antibodies specific for T cells (CD3), B cells (CD19) and monocytes (CD14). Results are shown in FIG. 24. Results expressed are percentage of monocytes that are also positive for the E antigen. In both subjects, although fresh cells could be infected, the detection of infection from frozen cells was much diminished, due in part to the increased background antibody staining on uninfected cells. Nonetheless, the same patterns of ADE were observed in both fresh and frozen cells. In the absence of significant infection, the efficiency of neutralization was difficult to assess using frozen cells.

Example 28

Antibody-Dependent Immune Enhancement and HIV

ADE has been postulated to be a major mechanism of pathogenesis in dengue virus infection (Halstead, S. B., "Pathogenesis of Dengue: Challenges to Molecular Biology," *Science* 239:476-481 (1988); Kliks et al., "Evidence that Maternal Dengue Antibodies are Important in the Development of Dengue Hemorrhagic Fever in Infants," *Am J Trop Med Hyg* 38:411-419 (1988), which are hereby incorporated by reference in their entirety), and thus it is a challenging hurdle to the development of dengue vaccines, which are usually designed for potentially protective antibody responses to all four dengue serotypes simultaneously (Halstead et al., "Dengue Virus: Molecular Basis of Cell Entry and Pathogenesis," *Vaccine* 23:849-856 (2005), which is hereby incorporated by reference in its entirety). ADE has also been noted for other flaviviruses, including West Nile virus, yellow fever virus and Japanese encephalitis virus, as well as alphavirus, poxvirus, and influenza virus (Halstead, S. B., "Pathogenesis of Dengue: Challenges to Molecular Biology," *Science* 239:476-481 (1988); Takeda et al., "Antibody-enhanced Infection by HIV-1 via Fc Receptor-mediated Entry," *Science* 242:580-583 (1988), which are hereby incorporated by reference in their entirety).

The protective immunity against HIV has been associated mostly with cellular immune responses, which are the current focus of the majority of candidate HIV vaccines. Nevertheless, neutralizing antibody responses clearly contribute to virologic control in vitro and in vivo. Thus, more active effort has been put into the development of immunogens that will stimulate a neutralizing antibody response. Whether such immunogens will also produce antibodies that will enhance HIV replication has been a lingering concern (Mascola et al., "Summary Report: Workshop on the Potential Risks of Antibody-dependent Enhancement in Human HIV Vaccine Trials," *AIDS Res Hum Retroviruses* 9:1175-1184 (1993); Burke, D. S., "Human HIV Vaccine Trials: Does Antibody-dependent Enhancement Pose a Genuine Risk?," *Perspect Biol Med* 35:511-530 (1992), which are hereby incorporated by reference in their entirety).

Some antibodies are evidently enhancing instead of neutralizing HIV replication. For instance, the level of ADE appears to increase over time in some patients with progressive HIV disease (Homsy et al., "Serum Enhancement of Human Immunodeficiency Virus (HIV) Infection Correlates with Disease in HIV-infected Individuals," *J Virol* 64:1437-1440 (1990); Takeda & Ennis, "FcR-mediated Enhancement of HIV-1 Infection by Antibody," *AIDS Res Hum Retroviruses* 6:999-1004 (1990); Takeda et al., "Distinction of Human Immunodeficiency Virus Type 1 Neutralization and Infection Enhancement by Human Monoclonal Antibodies to Glycoprotein 120," *J Clin Invest* 89:1952-1957 (1992), which are hereby incorporated by reference in their entirety). It is not clear whether the principal viral receptor, CD4, is indispensable for enhanced HIV replication. Some data showing that blocking CD4 did not prevent the enhancement of HIV infection (Homsy et al., "The Fc and Not CD4 Receptor Mediates Antibody Enhancement of HIV Infection in Human Cells," *Science* 244:1357-1360 (1989); Trischmann et al., "Lymphocytotropic Strains of HIV Type 1 When Complexed with Enhancing Antibodies Can Infect Macrophages via FcγRIII, Independently of CD4," *AIDS Res Hum Retroviruses* 11:343-352 (1995), which are hereby incorporated by reference in their entirety) indicates that viral receptor (CD4 molecules) may not be necessary for ADE. Furthermore, fibroblasts that are induced to express Fc receptor but lack CD4 can be infected by HIV (McKeating et al., "HIV Susceptibility Conferred to Human Fibroblasts by Cytomegalovirus-induced Fc Receptor," *Nature* 343:659-661 (1990), which is hereby incorporated by reference in its entirety). In contrast, others have shown that both CD4 and FcγR are necessary for ADE in the context of HIV replication (Takeda et al., "Two Receptors are Required for Antibody-dependent Enhancement of Human Immunodeficiency Virus Type 1 Infection: CD4 and FcγR," *J Virol* 64:5605-5610 (1990), which is hereby incorporated by reference in its entirety).

Different members of the FcγR family seem to play a role in the ADE of HIV infection. It is demonstrated that FcγRIII, not FcγRI or FcγRII, is mechanistically involved in ADE in macrophage but not in CD4 T cells (Homsy et al., "The Fc and Not CD4 Receptor Mediates Antibody Enhancement of HIV Infection in Human Cells," *Science* 244:1357-1360 (1989), which is hereby incorporated by reference in its entirety). However, in U937 cells devoid of FcγRIII, HIV infection can be enhanced by suboptimal concentration of neutralizing antibody; the ADE can be blocked by aggregated IgG, but not IgG-F(ab')$_2$ (Takeda et al., "Antibody-enhanced Infection by HIV-1 via Fc Receptor-mediated Entry," *Science* 242:580-583 (1988), which is hereby incorporated by reference in its entirety). Further experiments from the same group showed that ADE of HIV in U937 cells could be blocked by monoclonal antibody to FcγRI, but not to FcγRII (Takeda & Ennis, "FcR-mediated Enhancement of HIV-1 Infection by Antibody," *AIDS Res Hum Retroviruses* 6:999-1004 (1990), which is hereby incorporated by reference in its entirety).

Thus, the present invention can be adapted to screen enhancement and infectivity of HIV using cells expressing an appropriate Fcγ receptor, either FcγRI or FcγRIII, and anti-HIV antibodies.

Example 29

Screening of Monoclonal Antibodies

Figure 25:
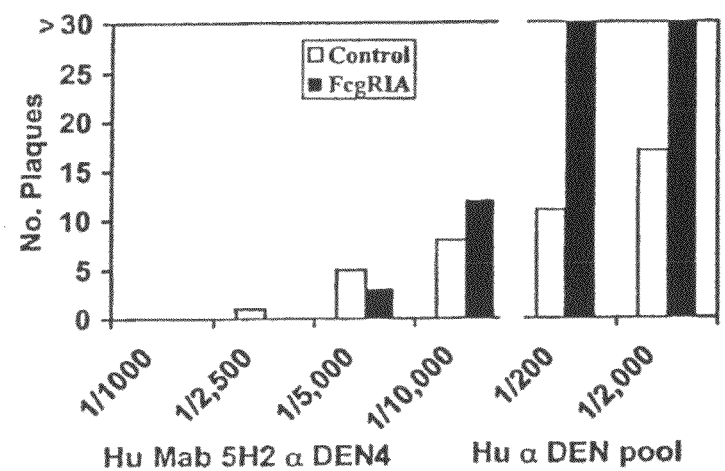
FIG. 25 is a graph of infectivity of DEN4 (H241 strain) and monoclonal antibody 5H2 ("Hu Mab 5H2 α DEN4") and pooled human DEN serum ("Hu α DEN pool"; control) in FcγRIA and control CV-1 cells. 5H2 strongly neutralized virus infectivity with similar efficiency in both FcγRIA and control cells at the dilutions used.

A panel of humanized chimpanzee monoclonal antibody against DEN4 have been prepared by Dr. C-J Lai and colleagues (National Institutes of Health). Antibody 5H2, a serotype-specific antibody likely directed to E domain III of DEN4, was tested using an assay of the present invention and found to strongly neutralize DEN4 in both FcγRIA and control cells, as shown in FIG. 25. Additional monoclonal antibodies (for example, from the NIH's humanized monoclonal antibody panel) will be examined using the assay of the present invention as they are characterized and made available.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of determining immune enhancement of virus infectivity comprising:
    exposing a first virion-antibody mixture comprising virion-antibody complexes to a first set of cells, wherein the cells do not express a native Fc receptor but comprise a bicistronic DNA construct that expresses both an Fc receptor γ-chain polypeptide and an Fc receptor α-subunit, with the Fc receptor γ-chain polypeptide being expressed in stoichiometric excess of the Fc receptor α-subunit, whereby the recombinant cells comprise a recombinant Fc receptor competent for both binding and uptake of virion-antibody complexes;
    measuring infectivity of the first virion-antibody mixture in the first set of cells;
    providing an infectivity standard; and
    comparing the measured infectivity to the infectivity standard, wherein an increase in infectivity relative to the infectivity standard indicates that antibodies in the first virion-antibody mixture promote immune enhancement.

2. The method according to claim 1, wherein said providing an infectivity standard comprises:
    exposing a second virion-antibody mixture to a second set of cells, wherein the second virion-antibody mixture is substantially similar to the first virion-antibody mixture and wherein the cells of the second set are substantially free of the recombinant Fc receptor; and
    measuring infectivity of the second virion-antibody mixture in the second set of cells.

3. The method according to claim 1, wherein said providing an infectivity standard comprises:
    exposing a second virion-antibody mixture that is substantially free of virion-antibody complexes to a second set of cells, wherein the second set of cells is substantially similar to the first set of cells; and
    measuring infectivity of the second virion-antibody mixture in the second set of cells.

4. The method according to claim 1 wherein the virion is selected from the group of Flaviviridae, Togaviridae, Retroviridae, Orthomyxoviridae, Paramyxoviridae, Arenaviridae, Bunyaviridae, Filoviridae, Rhabdoviridae, Picornaviridae, Herpesviridae, Reoviridae, and Coronaviridae.

5. The method according to claim 4 wherein the virion is selected from the group of dengue virus, West Nile virus, Japanese encephalitis virus, Kunjin virus, Murray Valley encephalitis virus, Uganda-S virus, yellow fever virus, Tick-borne encephalitis virus, hepatitis C virus, Louping-ill virus, Ross River virus, Semliki Forest virus, Sindbis virus, Western equine encephalitis virus, human immunodeficiency virus, Influenza A, Influenza B, respiratory syncytal virus, Lassa virus, Pichinde virus, Lokern virus, Rift Valley fever virus, Ebola virus, rabies virus, polio virus, Coxsackie B3 virus, Simplex virus, mammalian orthoreovirus, and feline infectious peritonitis virus.

6. The method according to claim 1 wherein the cells are mammalian cells.

7. The method according to claim 6 wherein the mammalian cells are selected from the group of monkey kidney cells, COS cells, CV-1 cells, Vero cells, LLC-MK2 cells, human adenocarcinoma SW13 cells, HeLa cells, endothelial cells, primary foreskin fibroblasts, liver Huh-7 cells, baby hamster kidney cells, and Chinese hamster ovary cells.

8. The method according to claim 1 wherein the receptor is an Fc receptor selected from the group of Fc$\alpha$R, Fc$\delta$R, Fc$\gamma$R, Fc$\epsilon$R, Fc$\alpha/\mu$, and FcRn.

9. The method according to claim 8 wherein the Fc receptor is an Fc$\gamma$R selected from the group of Fc$\gamma$RIA (CD64), Fc$\gamma$RIIA (CD32), Fc$\gamma$RIIIA (CD16), and Fc$\gamma$RIIB.

10. The method according to claim 1 wherein the antibody is selected from the group of IgA, IgG, IgD, IgM, and IgE.

11. The method according to claim 1 wherein the first virion-antibody mixture comprises virion exposed to either an antiserum obtained from a mammal immunized against a virus or a composition comprising a monoclonal antibody or binding fragment thereof.

12. The method according to claim 11 wherein the virus against which the mammal is immunized and the virion exposed to the antiserum are the same viral strain.

13. The method according to claim 11 wherein the virus against which the mammal is immunized and the virion exposed to the antiserum are different viral strains.

14. The method according to claim 11 wherein the mammal is a human.

15. The method according to claim 1 wherein said measuring comprises detecting presence of a non-structural protein or an envelope protein of the virion.

16. The method according to claim 15 wherein the virion is Dengue virus and said measuring comprises detecting presence of Dengue virus nonstructural protein NS-1 and/or envelope protein E.

17. The method according to claim 15 wherein said detecting is carried out by enzyme-linked immunosorbent assay and/or flow cytometry.

18. The method according to claim 1 wherein the cells of the first set further comprise a viral receptor.

19. A method of identifying a virus epitope implicated in immune enhancement of virus infectivity comprising:
performing the method according to claim 1 using an antibody known to bind specifically to a particular virus epitope to form the virion-antibody complexes,
wherein an increase in infectivity relative to the infectivity standard indicates that the virus epitope is implicated in immune enhancement of virus infectivity.

20. The method according to claim 1, wherein the bicistronic DNA construct comprises a promoter operably coupled to first and second DNA molecules and an internal ribosomal entry site located between the first and second DNA molecules, the first DNA molecule comprising a nucleotide sequence that encodes the Fc receptor $\gamma$-chain polypeptide and the second DNA molecule comprising a nucleotide sequence that encodes the Fc receptor $\alpha$-subunit.

21. The method according to claim 1, wherein the bicistronic DNA construct expresses the Fc receptor $\gamma$-chain polypeptide and the Fc receptor $\alpha$-subunit at about a 2:1 ratio.

22. The method according to claim 1, wherein the recombinant cells comprise the bicistronic DNA construct stably integrated into a genome thereof.

23. The method according to claim 1, wherein the recombinant cells express the recombinant Fc receptor at a cell surface concentration comparable to human peripheral blood monocytes or macrophages.

24. The method according to claim 1, wherein the recombinant cells express the recombinant Fc receptor at a cell surface concentration of about 30,000 to about 43,000 receptors per cell.

25. The method according to claim 1, wherein the recombinant cells express two or more recombinant Fc receptors.

26. The method according to claim 1, wherein the virion is a Dengue virion and the recombinant cells express a human Fc$\gamma$ receptor competent for both binding and uptake of Dengue virion-antibody complexes.

27. The method according to claim 26 wherein the human Fc$\gamma$ receptor is Fc$\gamma$RIA (CD64), Fc$\gamma$RIIA (CD32), Fc$\gamma$RIIIA (CD16), or Fc$\gamma$RIIB.

* * * * *